United States Patent
Sugimura

(10) Patent No.: US 11,369,095 B2
(45) Date of Patent: Jun. 28, 2022

(54) METHOD FOR REARING ANIMALS AND APPARATUS FOR REARING ANIMALS

(71) Applicant: TOYOTA BOSHOKU KABUSHIKI KAISHA, Aichi (JP)

(72) Inventor: Asako Sugimura, Aichi (JP)

(73) Assignee: TOYOTA BOSHOKU KABUSHIKI KAISHA, Aichi (JP)

( * ) Notice: Subject to any disclaimer, the term of this patent is extended or adjusted under 35 U.S.C. 154(b) by 352 days.

(21) Appl. No.: 16/287,012

(22) Filed: Feb. 27, 2019

(65) Prior Publication Data
US 2019/0261608 A1  Aug. 29, 2019

(30) Foreign Application Priority Data

Feb. 28, 2018  (JP) .............................. JP2018-035743
Feb. 13, 2019  (JP) .............................. JP2019-023958

(51) Int. Cl.
*A01K 67/02*  (2006.01)
*A01K 61/10*  (2017.01)

(52) U.S. Cl.
CPC .............. *A01K 67/02* (2013.01); *A01K 61/10* (2017.01)

(58) Field of Classification Search
CPC ........ A01K 5/0114; A01K 5/02; A01K 61/85; A01K 7/04; A01K 61/80; A01K 5/0275; A01K 5/0291; A01K 67/02; A01K 61/10
USPC ............. 119/51.01, 51.02, 212, 51.04, 51.11
See application file for complete search history.

(56) References Cited

U.S. PATENT DOCUMENTS

| | | | | |
|---|---|---|---|---|
| 3,473,509 A | * | 10/1969 | Mitsutake | .............. A01K 61/59 119/205 |
| 2005/0190652 A1 | * | 9/2005 | Marhic | ................ G04G 9/0076 368/15 |
| 2010/0330251 A1 | * | 12/2010 | Weakley | .............. A23K 20/158 426/601 |
| 2015/0010699 A1 | | 1/2015 | Vellrath | |
| 2017/0107482 A1 | * | 4/2017 | Yamamoto | ............. G01N 33/48 |
| 2018/0055931 A1 | * | 3/2018 | Yamamoto | ............. A61H 99/00 |

FOREIGN PATENT DOCUMENTS

| | | |
|---|---|---|
| CN | 102214262 A | 10/2011 |
| CN | 104304097 A * | 1/2015 |
| CN | 106577559 A | 4/2017 |

(Continued)

OTHER PUBLICATIONS

Matsumoto et al., "GOTIC2: A Program for Computation of Oceanic Tidal Loading Effect," J Geodetic Society Japan, 47(1), 2001, pp. 243-248.

(Continued)

*Primary Examiner* — Peter M Poon
*Assistant Examiner* — Jeffrey R Larsen
(74) *Attorney, Agent, or Firm* — Greenblum & Bernstein, P.L.C.

(57) ABSTRACT

The method for rearing an animal according to the present invention includes: grasping a tide-generating force; and feeding, to the animal, foods varying in fat ingredient content according to the variation level of the tide-generating force. In addition, the apparatus for rearing an animal according to the present invention is provided with a food feeding means for feeding, to the animal, foods varying in fat ingredient content according to the variation level of a tide-generating force.

9 Claims, 12 Drawing Sheets

(56) References Cited

FOREIGN PATENT DOCUMENTS

CN    107396878 A    11/2017
JP    2013-215099    10/2013
JP    2015-012809    1/2015

OTHER PUBLICATIONS

Lyard et al., "Modelling the global ocean tides: modern insights from FES2004," Ocean Dynamics, 56, Sep. 27, 2006, pp. 394-415.
Office Action issued in related U.S. Appl. No. 15/273,126, dated Oct. 4, 2018.
Office Action issued in CN Counterpart Patent Appl. No. 201910152312.7, dated Feb. 3, 2021, along with an English translation thereof.
Office Action issued in Japan Counterpart Patent Appl. No. 2019-023958, dated Apr. 26, 2022, along with an English translation thereof.

* cited by examiner

Example 4

METHOD FOR REARING ANIMALS AND APPARATUS FOR REARING ANIMALS

CROSS REFERENCE TO RELATED APPLICATION

The present application claims priority under 35 USC § 119 to Japanese Patent Application No. 2018-35743 filed on Feb. 28, 2018, and Japanese Patent Application No. 2019-23958 filed on Feb. 13, 2019, the disclosures of which are hereby expressly incorporated by reference in their entirety.

BACKGROUND OF THE INVENTION

(1) Field of the Invention

The present invention relates to a method and an apparatus for rearing an animal. More specifically, the present invention relates to a method and an apparatus for rearing an animal, which can control the degree of increase in body weight or fat quantity according to expectation by utilizing the variation level of a tide-generating force which can be easily grasped.

(2) Description of Related Art

In various biological production sites, sufficient standardization of production works has not been achieved yet, and, actually, there are many cases of relying on the experiences and intuition of producers according to the production purpose, and further facilitation of production works is thus awaited. The biological production management apparatus and system of JP 2013-215099 A include not only plants but also animals such as livestock as targets for production management. The biological production management apparatus and system are required to manage an animal husbandry schedule based on the type of animal (livestock) to be produced, work information, and the like.

In addition, JP 2015-12809 A discloses a method for feeding a pet food for suppressing the accumulation of body fat, that is, a method for rearing a pet.

SUMMARY OF THE INVENTION

However, the biological production management apparatus and system of JP 2013-215099 A require equipment that always acquires various kinds of information on the actual situation of the production sites, the animals to be produced, and the like one by one. Such a system will be used to rear animals according to a predetermined production purpose based on the acquired various kinds of information. Therefore, the rearing of animals with a controlled degree of increase in body weight of an animal or a controlled fat quantity is accompanied with such inconvenience that the operation of the apparatus and system becomes exaggerated.

Further, the pet food feeding method described in JP 2015-12809 A requires labor to feed a predetermined pet food product twice a day according to a predetermined method. Therefore, the rearing of healthy pets with suppressed accumulation of body fat disadvantageously requires much time and effort on a daily basis.

The present invention has been made in view of the above actual situation, and it is an object of the present invention to provide a method and an apparatus for rearing an animal, which can control the degree of increase in body weight or fat quantity according to expectation by utilizing the variation level of a tide-generating force that can be easily grasped.

As a result of earnest studies, the present inventors have found that the variation level of a tide-generating force unexpectedly affects the degree of increase in body weight of an animal or the accumulation of fat quantity, and that the degree of increase in body weight or fat quantity can be controlled according to expectation depending on the variation level of the tide-generating force, thus have completed the present invention. The present invention which solves the above problems is as follows.

(1) A method for rearing an animal, which controls an increase in body weight or fat, the method comprising: grasping a tide-generating force; and feeding, to the animal, foods varying in fat ingredient content according to the variation level of the tide-generating force.

(2) The method for rearing an animal according to (1), wherein, in order to grasp the tide-generating force, the following steps are carried out: preliminarily acquiring future tidal information which periodically varies within a predetermined period; and determining the variation level of the tide-generating force within a unit period with reference to the tidal information.

(3) The method for rearing an animal according to (2), wherein, after grasping the tide-generating force, the following steps are carried out: extracting a first timing with a relatively high variation level of the tide-generating force or a second timing with a relatively low variation level of the tide-generating force, from within the predetermined period during which the tidal information has been acquired; and then feeding, to the animal, the foods varying in the fat ingredient content between at the first timing and at a timing other than the first timing or feeding, to the animal, the foods varying in the fat ingredient content between at the second timing and at a timing other than the second timing.

(4) The method for rearing an animal according to (3), wherein the first timing is a timing of a spring tide; and, at the timing of the spring tide, the animal is fed on the food having the fat ingredient content higher than that at a timing other than the spring tide.

(5) The method for rearing an animal according to (3), wherein the second timing is a timing of a neap tide; and, at the timing of the neap tide, the animal is fed on the food having the fat ingredient content higher than that at a timing other than the neap tide.

(6) The method for rearing an animal according to any one of (2) to (5), wherein the tidal information is the prediction of a periodical variation for a gravity acceleration linked with a variation in solid tide and/or for a tide level linked with a variation in marine tide.

(7) An apparatus for rearing an animal, which controls an increase in body weight or fat, the apparatus comprising a food feeding means for feeding, to the animal, foods varying in fat ingredient content according to the variation level of a tide-generating force.

(8) The apparatus for rearing an animal according to (7), further comprising a tide-generating force grasping means for determining the variation level of the tide-generating force, wherein the tide-generating force grasping means has: a tidal information acquisition part for preliminarily acquiring future tidal information which periodically varies within a predetermined period; and a tide-generating force variation value calculation part for calculating the variation level of the tide-generating force within a unit period with reference to the tidal information.

(9) The apparatus for rearing an animal according to (8), further comprising a specific timing extraction part for extracting a first timing showing a relatively large variation value of the tide-generating force or a second timing showing a relatively small variation value of the tide-generating force, from within the predetermined period during which the tidal information has been acquired, wherein the food feeding means is intended to feed, to the animal, the foods varying in the fat ingredient content between at the first timing extracted by the specific timing extraction part and at a timing other than the first timing or to feed, to the animal, the foods varying in the fat ingredient content between at the second timing and at a timing other than the second timing.

(10) The apparatus for rearing an animal according to (9), wherein the first timing is a timing of a spring tide; and the food feeding means is intended to feed, at the timing of the spring tide, the animal on the food having the fat ingredient content higher than that at a timing other than the spring tide.

(11) The apparatus for rearing an animal according to (9), wherein the second timing is a timing of a neap tide; and the food feeding means is intended to feed, at the timing of the neap tide, the animal on the food having the fat ingredient content higher than that at a timing other than the neap tide.

(12) The apparatus for rearing an animal according to any one of (8) to (11), wherein the tidal information is the prediction of a periodical variation for the gravity acceleration linked with a variation in solid tide and/or for the tide level linked with a variation in marine tide.

The method for rearing an animal according to the present invention involves feeding, to an animal, foods varying in fat ingredient content according to the variation level of a tide-generating force. So, the degree of increase in body weight of the animal or the quantity of fat accumulated in the body thereof can be changed. Therefore, the animal can be reared according to expectation, with the intention of an expected degree of increase in body weight or fat quantity. As a result, it is possible to improve the efficiency of rearing the animal, to shorten the rearing period, and to suppress the rearing cost.

In addition, when preliminarily acquiring future tidal information to grasp the tide-generating force, it is possible to utilize a periodic variation in tide-generating force for choosing the timings for feeding foods varying in fat ingredient content, and thus to easily determine future timings for feeding the foods to the animal, as planned.

In addition, when extracting a first timing with a relatively large variation in tide-generating force or a second timing with a relatively low variation in tide-generating force and feeding, to the animal, foods varying in fat ingredient content between at the first timing and at a timing other than the first timing or between at the second timing and at a timing other than the second timing, it is possible to more reliably change the degree of increase in body weight of the animal or the quantity of fat accumulated in the body thereof.

In addition, when, at a timing of a spring tide which is the first timing, the animal is fed on a high-fat food having the fat ingredient content higher than that at a timing other than the spring tide, it is possible to suppress the degree of increase in body weight of the animal and the quantity of fat accumulated in the body thereof, although the animal is fed on the high-fat food. That is, it is possible to suppress the degrees of increase in body weight and fat quantity as compared with when similarly feeding the high-fat food at a timing of a neap tide. Therefore, when it is expected or intended to suppress the increase in body weight or fat quantity while the animal should be fed on such a high-fat food, it is possible to easily rear the animal as expected.

On the other hand, when, at a timing of a neap tide which is the second timing, the animal is fed on a high-fat food having the fat ingredient content higher than that at a timing other than the neap tide, it is possible to increase the degree of increase in body weight of the animal and the quantity of fat accumulated in the body thereof. That is, it is possible to increase the degrees of increases in body weight and fat quantity as compared with when similarly feeding the high-fat food at the timing of the spring tide. Therefore, when it is expected or intended to increase the body weight or fat quantity through feeding such a high-fat food to the animal, it is possible to easily rear the animal as expected.

When the gravity acceleration linked with a variation in solid tide is used as the tidal information, the solid tide relies mainly on the topography of a target point, and thus a calculated value of the gravity acceleration can be obtained with high accuracy. Therefore, it is possible to increase the accuracy of determining the variation level of the tide-generating force. In addition, when the tide level linked with a variation in marine tide is used as the tidal information, tide level prediction data can be easily obtained from various related organizations. Therefore, the animal can be easily reared as expected.

Since the apparatus for rearing an animal according to the present invention is provided with a food feeding means for feeding, to an animal, foods varying in fat ingredient content according to the variation level of a tide-generating force, it is possible to change the degree of increase in body weight of the animal or the quantity of fat accumulated in the body thereof by feeding the foods to the animal via the food feeding means. Therefore, the animal can be reared as expected, with the intention of an expected degree of increase in body weight or fat quantity. As a result, it is possible to improve the efficiency of rearing the animal, to shorten the rearing period, and to suppress the rearing cost.

Also, when the apparatus for rearing an animal is provided with a tide-generating force grasping means having the tidal information acquisition part and the tide-generating force variation value calculation part for calculating (obtaining) the variation level of the tide-generating force, it is possible to easily determine future timings for feeding, to the animal, foods varying in fat ingredient content, as planned.

In the case where the apparatus is provided with the specific timing extraction part, the animal is fed on foods varying in fat ingredient content between at the first timing and at a timing other than the first timing, or between at the second timing and at a timing other than the second timing. So, it is possible to more reliably change the degree of increase in body weight of the animal or the quantity of fat accumulated in the body thereof.

When the apparatus for rearing an animal is provided with a food feeding means for feeding, at a timing of a spring tide which is the first timing, the animal on a high-fat food having the fat ingredient content higher than that at a timing other than the spring tide, it is possible to suppress the degree of increase in body weight of the animal and also to suppress the quantity of fat accumulated in the body thereof, although the animal is fed on the high-fat food. That is, the degrees of increases in body weight and fat quantity can be suppressed as compared with when the apparatus has a food feeding means for similarly feeding the high-fat food at a timing of a neap tide. Therefore, when it is expected or intended to suppress the increase in body weight or fat quantity while the animal should be fed on such a high-fat food, it is possible to easily rear the animal.

On the other hand, when the apparatus for rearing an animal is provided with a food feeding means for feeding, at a time of a neap tide which is the second timing, the animal on a high-fat food having the fat ingredient content higher than that at a timing other than the neap tide, it is possible to increase the degree of increase in body weight of the animal and the quantity of fat accumulated in the body thereof. That is, the body weight and fat quantity can be increased as compared with when the apparatus has a food feeding means for similarly feeding the high-fat food at the timing of the spring tide. Therefore, when it is expected or intended to increase the body weight or fat quantity through feeding such a high-fat food to the animal, it is possible to easily rear the animal.

In addition, when the tide-generating force grasping means uses the gravity acceleration or the tide level as the tidal information, it is possible to obtain the same effect as in the case of carrying out the method for rearing an animal described above.

DETAILED DESCRIPTION OF PREFERRED EMBODIMENTS

Hereinafter, the present invention will be described in detail.

[1] Method for Rearing Animal

Figure 1:
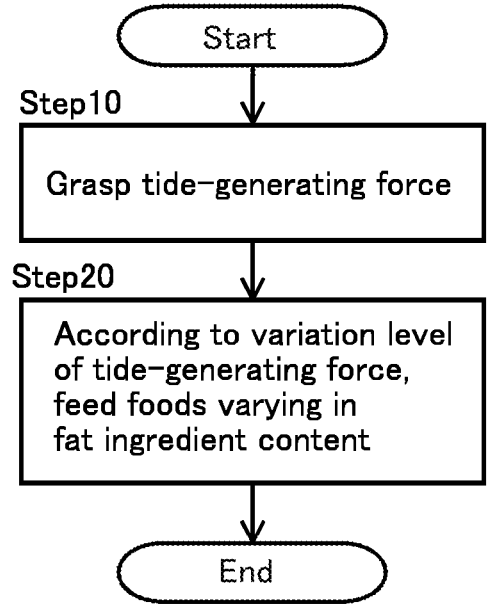
FIG. 1 is a flowchart for explaining a method for rearing an animal.

The method for rearing an animal according to the present invention is a method for rearing an animal, which controls an increase in body weight or fat, as shown in FIG. 1, the method comprising: grasping a tide-generating force (Step 10); and feeding, to the animal, foods (123a, 123b) varying in fat ingredient content according to the variation level (T1 to T12) of the tide-generating force (Step 20) (see FIGS. 4 and 6 to 8).

The animal in the present invention is not particularly limited, and specific examples thereof include mammals (including humans), birds, reptiles, amphibians, fish, and invertebrates.

1. Step of Grasping Tide-Generating Force

Generally, the tide-generating force is grasped based on information associated with tidal phenomena such as the relative gravity acceleration (theoretical value), meteorological data (atmospheric pressure, tide name, tide level, tidal difference etc.), ecliptic longitudinal difference (ecliptic longitudinal difference between the sun and the moon), age of the moon, or the like as an indicator. Further, the variation level of the tide-generating force can be determined based on the thus-grasped tide-generating force. The "grasp of a tide-generating force" according to the present embodiment means estimating a periodic variation in tide-generating force and the variation level thereof within a predetermined period during which the animal is scheduled to be reared in future, thereby grasping the tide-generating force.

In the present embodiment, the length of the predetermined period for rearing an animal is not particularly limited, and is appropriately adjusted according to the type of animal. Specifically, the "predetermined period" can be set to 6 hours, 12 hours, 24 hours, 48 hours, 72 hours, 1 week, 2 weeks, 4 weeks, 3 months, 6 months, 1 year, or the like. In order to grasp the tide-generating force, the tidal information within a predetermined period from the scheduled start date of rearing of the animal to the end date only has to be acquired as appropriate.

Figure 2:
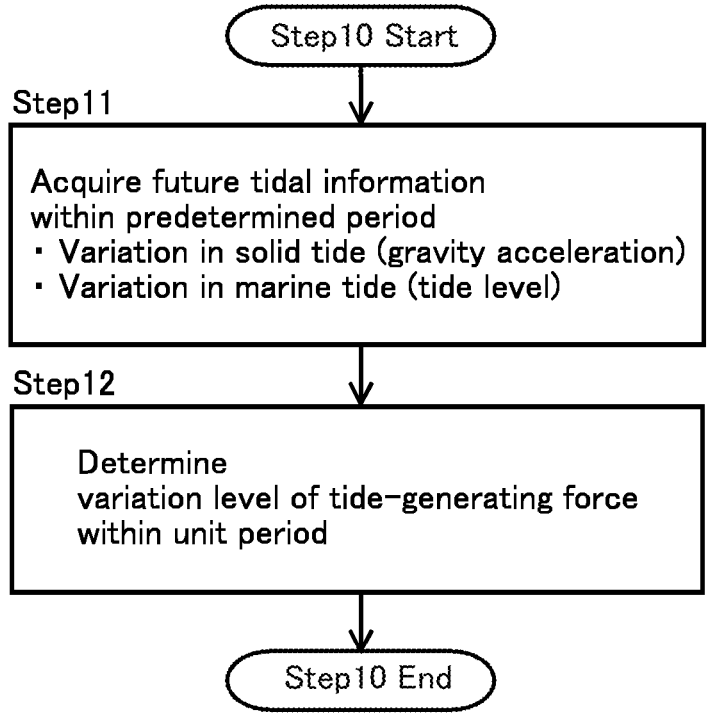
FIG. 2 is a flowchart for explaining a step of grasping a tide-generating force.

For example, as shown in FIG. 2, in Step 10 of grasping the tide-generating force, there are carried out Step 11 of preliminarily acquiring future tidal information which periodically varies within a predetermined period during which the animal is scheduled to be reared and then Step 12 of determining the variation level of the tide-generating force within a unit period with reference to the tidal information. As described above, before the start of rearing of the animal, future tidal information is preliminarily acquired, and the variation level of the future tide-generating force is determined based on the tidal information. According to the variation level of the tide-generating force, timings for feeding, to the animal, foods varying in fat ingredient content are planned preliminarily. Therefore, future timings for feeding the foods to the animal can be easily determined according to the periodic variation in tide-generating force, as planned.

As the tidal information, there is known information based on a solid tide based on an elastic variation in solid portion on the ground, a marine tide appearing as a variation in marine tide level, or an atmospheric tide based on a variation in atmospheric pressure linked with the variation in marine tide level. Among these, it is preferable to refer to the solid tide specifically, it is preferable to use tidal information on the gravity acceleration linked with the variation in solid tide In this case, Step 11 of preliminarily acquiring the tidal information is carried out by acquiring the prediction of a future periodic variation in gravity acceleration (see FIG. 2).

The variation in gravity acceleration is thought to occur periodically according to the elastic variation in solid portion on the ground, and thus can be calculated based on the topographical information of an animal rearing point, relying mainly on the topography of the animal rearing point. Since the topography cannot be easily deformed as compared with the sea level or the atmosphere, the variation in solid tide is predicted easily and more accurately. It is preferable to use the gravity acceleration linked with the solid tide as the tidal information, because highly accurate calculation results can be applied to a wide area on the ground, thereby enhancing the accuracy of grasping a future tide-generating force.

As another preferable example used as the tidal information, tidal information on the tide level linked with the variation in marine tide can also be used. That is, Step 11 of preliminarily acquiring tidal information is carried out by acquiring the prediction of a future periodic variation in tide level (see FIG. 2).

Since the variation in tide level is information that closely affects human life, prediction data concerning the information on the variation in tide level can be easily obtained from various marine management related organizations. It is preferable to use the tide level linked with the marine tide as the tidal information, in view of such simplicity.

The tidal information can be acquired by calculating the gravity acceleration for the solid tide or by appropriately determining the forecast of the variation in tide level for the marine tide. More preferably, it is possible to acquire a plurality of kinds of tidal information and to combine them for use.

Among the above ones, in the method for rearing an animal according to the present invention, from the viewpoint that the level of the tide-generating force and its cycle can be easily predicted, it is preferable to use the gravity acceleration linked with the solid tide as the tidal information to be acquired for grasping the tide-generating force, and to use the relative gravity acceleration as an indicator representing the gravity acceleration. Also, the relative gravity acceleration and the tide name, ecliptic longitudinal difference or age of the moon may be combined and used as an indicator.

Here, the relative gravity acceleration (RGA) means a relative value of the gravity acceleration with the standard gravity acceleration ($1G=9.80665\times10^8$ μGal) as the reference (zero point). This relative gravity acceleration can be calculated by utilizing a publicly-available solid tidal force prediction program. Specifically, by inputting various pieces of information on the position (latitude and longitude) of an execution site, date, and time into the solid tidal force prediction program, the relative gravity acceleration at the target point and the change thereof with time can be calculated. As the solid tidal force prediction program, for example, the tide prediction system "GOTIC2" (http://www.miz.nao.acjp/staffs/nao99/) or the like can be used.

When the above relative gravity acceleration is used as the indicator of gravity acceleration (and thus tide-generating force), prediction data on the change in relative gravity acceleration with time within a predetermined period scheduled to rear an animal, i.e., the relative gravity acceleration along the time axis within a predetermined period is obtained.

Next, in Step 12, the variation level of the tide-generating force during the unit period is determined with reference to the tidal information within the predetermined period preliminarily obtained in Step 11.

The "unit period" may be appropriately selected based on the prediction data on the tide-generating force obtained from the tidal information including the (relative) gravity acceleration, the tide level, and the like. Specifically, the "unit period" may be a period corresponding to one cycle, several cycles, or several tens of cycles in which the tide-generating force varies.

The variation level of the tide-generating force is determined from the above prediction data, for example, as a difference (maximum displacement) between the maximum value and the minimum value of the relative gravity acceleration within such a time that one cycle is regarded as the unit period, a total variation amount (total displacement amount), or the like. Thus, with reference to the tidal information periodically varying within the predetermined period, the data on the variation level of the tide-generating force obtained for each unit time can be accumulated and stored.

When the tide name is used as the indicator of tide-generating force to grasp the tide-generating force, it can be predicted that the variation level of the tide-generating force becomes higher in the order of the tide names: neap tide, nagashio (tide with a low tidal difference), wakashio (tide with an increasing tidal difference in a period from a neap tide toward a spring tide), half tide, and spring tide. There can be used the tide names given by the Japan Meteorological Agency or MIRC (Japan Hydrographic Association Marine Information Research Center). For example, the prediction data in a short-to-long predetermined period can be easily obtained, for example, based on data from the Japan Meteorological Agency (http://www.jma.go.jp/jma/index.html), data from the Japan Hydrographic Association Marine Information Research Center, etc.

When the ecliptic longitudinal difference is used as the indicator of the tide-generating force to grasp the tide-generating force, it can be thought the variation level of the tide-generating force is theoretically is higher at a timing when the ecliptic longitudinal difference is closer to 0° (360°) or 180°, and is lower at a timing when the ecliptic longitudinal difference is closer to 90° or 270° in the cycle of ecliptic longitudinal difference (0° to 360°). With respect to this indicator, the prediction data in a short-to-long predetermined period can be easily obtained, for example, from the Ephemeris Computation Office (http://eco.mt-k.nao.ac.jp/koyomi/) of the National Astronomical Observatory of Japan.

When the age of the moon is used as the indicator of tide-generating force to grasp the tide-generating force, it can be thought that the variation level of the tide-generating force is theoretically higher as the age is closer to 0 (30) or 15.0, and is lower as the age is closer to 7.5 or 22.5 in the cycle of the age (0 to 30). With respect to this indicator, the prediction data in a short-to-long predetermined period can be easily obtained, for example, from the Ephemeris Computation Office (http://eco.mtk.nao.acjp/koyomi/) of the National Astronomical Observatory of Japan or a general moon age calendar.

2. Food feeding according to variation level of tide-generating force After Step 10 of grasping the tide-generating force, Step 20 of feeding, to the animal, foods varying in fat ingredient content according to the variation level of the tide-generating force is carried out (see FIG. 1).

The "food" according to the present invention is not particularly limited, and refers to a substance which is fed in order to maintain the life of the above animal and functions as a nutrition for an animal, in accordance with a general meaning. The method of feeding the food is not particularly limited, and the food is usually ingested from the mouth of the animal, for example, by eating and drinking.

The fat ingredient contained in the food is not particularly limited, and refers to all of fat ingredients which are regarded as one of nutrients and ingredients also called lipid in addition to "fat", in accordance with a general meaning. The fat ingredients are, for example, oil and fat which are liquid at ordinary temperature and glycerin esters of fatty acids which are solid at ordinary temperature, and include ingredients composed of lipids such as saturated fatty acids, monounsaturated fatty acids, and polyunsaturated fatty acids.

Specific examples of fat ingredients include esters of fatty acids and glycerin typified by triglycerides, diglycerides, and monoglycerides. Fatty acids are each composed of a lipid such as a linear or branched, saturated or unsaturated carboxylic acid or the like having 10 to 28 carbon atoms. More specifically, examples of the fat ingredients include vegetable fat ingredients such as soybean, corn, sunflower, rapeseed, canola, cottonseed, olive, safflower, and sesame seed; animal fat ingredients such as beef tallow and lard; nut-based fat ingredients such as coconut, palm, palm kernel, and peanuts; milk fat ingredients such as butter and margarine; lecithin; and fish oil.

In addition, the food may contain, for example, one of the above-mentioned fat ingredients, or may contain two or more thereof. The food is not particularly limited depending on the (total) content of the above-mentioned fat ingredients. When the total weight of the food is taken as 100% by weight, the fat ingredient content can be about 1.0 to 60.0% by weight, preferably about 3.0 to 40.0% by weight.

Further, the "foods varying in fat ingredient content" of the present invention can be determined, for example, based on the weight ratio of the one food based on the (total) weight of its fat ingredients per unit weight. For example, it means foods in which the (total) weight of the fat ingredients of the other food is about 2 to 15 times, preferably about 4 to 10 times, more preferably about 6 to 9 times the reference value of the one food.

As an example of the embodiment in which Step 20 of "feeding, to the animal, foods varying in fat ingredient content according to the variation level of the tide-generating force" is carried out, a method which will be described below can be indicated. First, the data on the "variation level of the tide-generating force" is classified into either high or low with reference to the stored data on the "variation level of the tide-generating force" for each unit period grasped by carrying out Step 10 of grasping the tide-generating force. Specifically, unit periods that are classified as having a relatively high variation level of the tide-generating force are grasped, from within a predetermined period for rearing the animal. Further, based on the classified unit periods, timings with a high variation level of the tide-generating force including a plurality of unit periods are grasped. Or, similarly, unit periods that are classified as having a relative low variation level of the tide-generating force and further timings with a low variation level of the tide-generating force may be grasped. Then, depending on whether each of the timings for feeding foods to the animal belongs to the timing with a relatively high or low variation level of the tide-generating force, two kinds of foods having different, i.e., high and low, fat ingredient contents may be fed to the animal.

The number for classifying the variation levels of the tide-generating force is not particularly limited as long as it is the minimum number, two, or more, and the variation levels may be classified into more than two groups. Preferably, the variation levels can be classified into about two or three groups. The method of classifying the variation levels of the tide-generating force is not particularly limited as long as the variation levels can be classified into two or more groups. For example, it is possible to set a threshold value for the variation levels of the tide-generating force and to classify the variation levels into high or low, or high, medium, or low.

Also, it is possible to specify timings at which the variation level of the tide-generating force is relatively high (or relatively low) and to classify the specified timings from timings other than the specified timings, at which the variation level of the tide-generating force is relatively lower (or higher) than that at the specified timings.

The foods to be fed to the animal according to the classified variation levels of the tide-generating force may have more than two types of fat ingredient contents. That is, as long as the fat ingredient contents vary depending on whether high or low, the number of different fat ingredient contents is not particularly limited. Different fat ingredient contents may be prepared in a number according to the number of the groups for classification of the variation levels of the tide-generating force.

Specific examples of the method of "feeding, to the animal, foods varying in fat ingredient content according to the variation level of a tide-generating force" include a method of feeding the food having a high fat ingredient content at a timing when the "variation level of the tide-generating force" is classified into "high" group and feeding the food having a low fat ingredient content at a timing when the "variation level of the tide-generating force" is classified into "low" group, within the predetermined period for rearing the animal. Conversely, there may be employed a method of feeding a food having a high fat ingredient content at a timing with a "low" "variation level of the tide-generating force" and feeding the food having a low fat ingredient content at a timing with a "high" "variation level of the tide-generating force", within a predetermined period for rearing the animal.

In addition, when the "variation levels of the tide-generating force" are classified into three groups of high, medium and low, it is possible to feed three kinds of foods varying in fat ingredient content according to the three groups for classification or to feed two of the three as appropriate. That is, it is possible to use a method of determining the timings for feeding foods varying in fat ingredient content to the animal according to the variation level of a tide-generating force.

Figure 3:
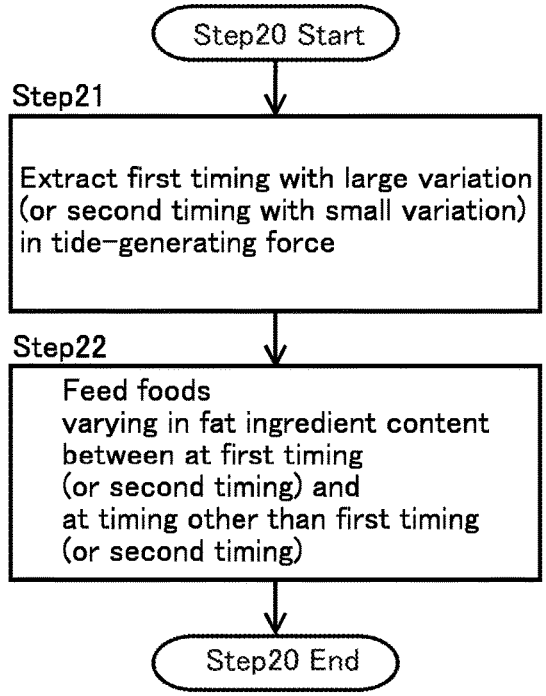
FIG. 3 is a flowchart for explaining a step of feeding foods according to a variation in tide-generating force.

As another example of the embodiment in which Step 20 is carried out, a method which will be described below can be indicated. Specifically, in order to execute the above Step 20, preferably, there is carried out Step 21 of extracting the first timing at which the variation level of the tide-generating force is relatively high or the second timing at which the variation level of the tide-generating force is relatively low, from within the predetermined period during which the tidal information has been acquired, as shown in FIG. 3. Thereafter, there is carried out Step 22 of feeding, to the animal, foods varying in fat ingredient content between at the first timing and at a timing other than the first timing, or between at the second timing and at a timing other than the second timing.

For example, in order to carry out Step 21 of extracting the first timing, it is also possible to specify a timing at which the difference between the maximum value and the minimum value of the gravity acceleration is relatively large, for example, within one cycle, from within the predetermined period during which the tidal information such as gravity acceleration has been obtained, and to extract the specified timing as the first timing. Alternatively, an appropriate group of unit periods including the specified one cycle, for example, a period of several cycles may be extracted as the first timing. Alternatively, the specified time combined with any other tidal information may be extracted as the first timing. Examples of the other tidal information can include the timing indicated by the tide name such as spring tide or half tide, the timing at which the ecliptic longitudinal difference is 0° (360°) or 180°, and the timing at which the age of the moon is close to 0 (30) or 15.0. A timing at which the other tidal information overlaps with a timing at which the difference between the maximum value and the minimum value is relatively large may be extracted as the first timing.

Similarly as in the case of extracting the first timing, Step 21 of extracting the second timing may be carried out. In this case, examples of the other tidal information can include the timing indicated by the tide name such as neap tide or nagashio, the timing when the ecliptic longitudinal difference is 90° or 270°, and the timing at which the age is close to 7.5 or 22.5.

Next, in order to carry out Step 22 of feeding foods varying in fat ingredient content between at the first timing and at a timing other than the first timing, it is necessary that the fat ingredient content of the food to be fed at the first timing be different from that of the food to be fed at a timing other than the first timing, and it is preferable to feed, at the first timing, a food having the fat ingredient content relatively higher than that at the timing other than the first timing. Or, similarly in the case of carrying out Step 22 of feeding foods varying in fat ingredient content between at the second timing and at a timing other than the second timing, it is preferable to feed, at the second timing, a food having the fat ingredient content relatively higher than that at the timing other than the second timing.

Thus, by extracting the first timing at which the variation in tide-generating force is relatively large and feeding, to the animal, foods varying in fat ingredient content between at the first timing and at a timing other than the first timing, the degree of increase in body weight of the animal or the quantity of fat accumulated in the body thereof can be more reliably changed. Similarly in the case of extracting the second timing at which the variation in tide-generating force is relatively small and feeding, to the animal, foods varying in fat ingredient content between at the second timing and at a timing other than the second timing, the degree of increase in body weight of the animal or the quantity of fat accumulated in the body thereof can be more reliably changed.

More preferably, the above method can be implemented by [1] a method of feeding a food having a high fat ingredient content to an animal at the first timing with a relatively high variation level of the tide-generating force (for example, at a timing of a spring tide), for example, based on prediction data on the tide-generating force grasped. Also, the above method can be implemented by [2] a method of feeding a food having a high fat ingredient content to an animal at the second timing with a relatively low variation level of the tide-generating force (for example, at a timing of a neap tide), for example, based on prediction data on the tide-generating force grasped.

More specifically, as a timing with a relatively high variation level of the tide-generating force, with reference to a variation in relative gravity acceleration (value indicating the variation level of the obtained tide-generating force), for example, using, as an index, the fact that the variation within 24 hours which is a unit period is 190 μGal or more, preferably 200 μGal or more, or more preferably 210 μGal or more, the timing may be specified. Moreover, the specified timing may be extracted as the first timing, and a group of identified timings whose tide name is a spring tide and includes the specified timing may be extracted as the first timing. Alternatively, similarly, as a timing with a relatively low variation level of the tide-generating force, with reference to a variation in relative gravity acceleration (value indicating the variation level of the obtained tide-generating force), for example, using, as an index, the fact that the variation within 24 hours which is a unit period is 190 μGal or less, preferably 180 μGal or less, or more preferably 170 μGal or less, the timing may be specified. Moreover, the specified timing may be extracted as the second timing, and a group of specified timings whose tide name is a neap tide and includes the specified timing may be extracted as the second timing.

[2] Apparatus for Rearing Animal

Figure 4:
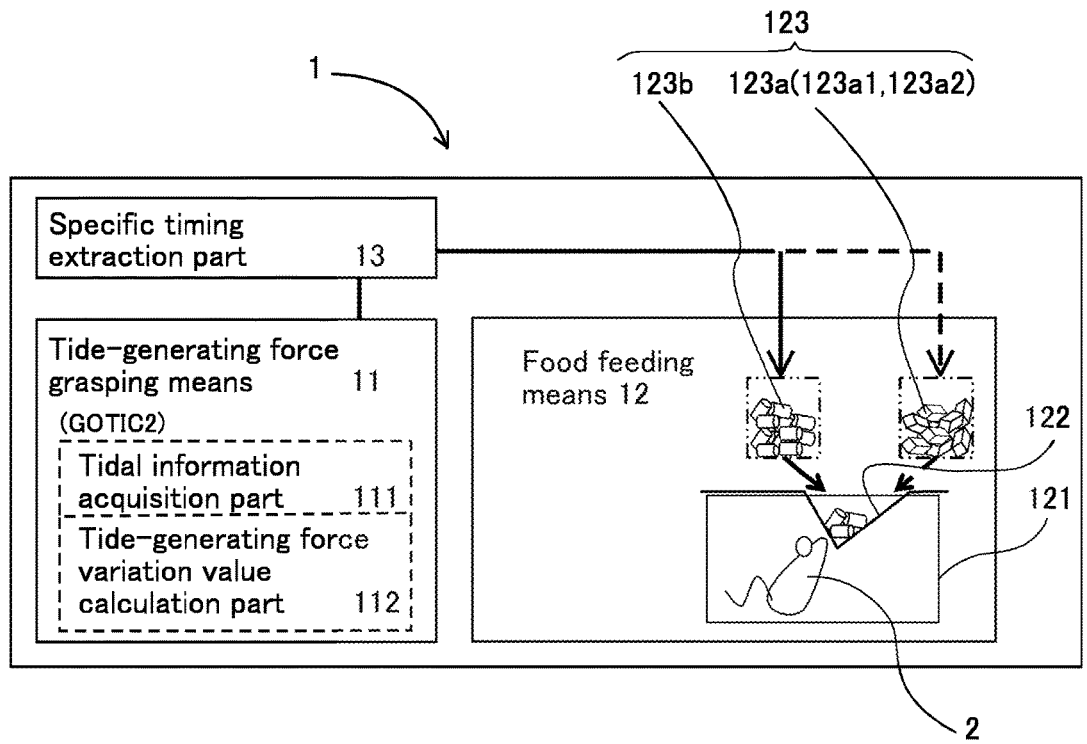
FIG. 4 is a view for explaining an apparatus for rearing an animal according to an Example.
Figure 6:
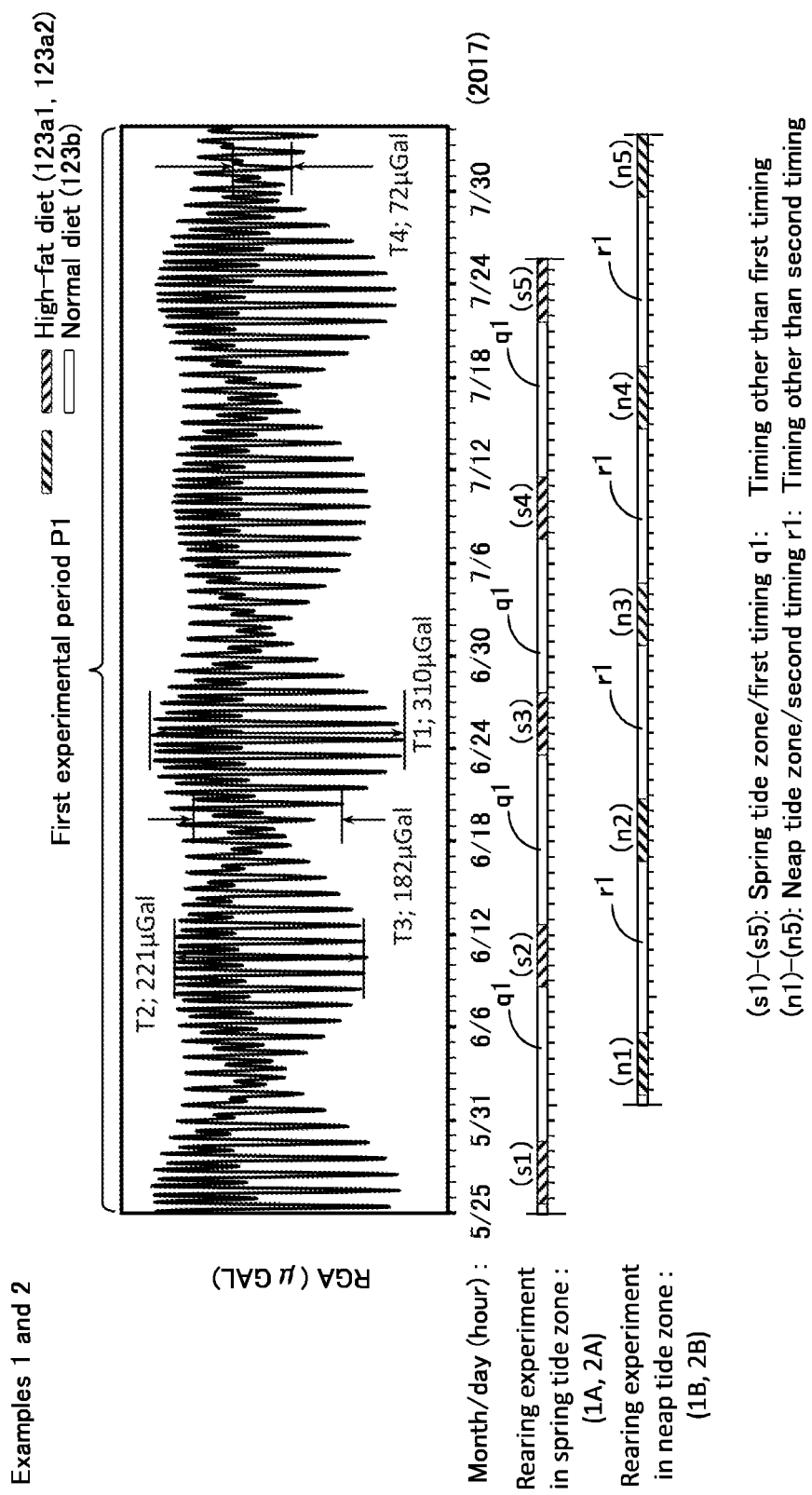
FIG. 6 is a view for explaining rearing experiments in a spring tide zone and a neap tide zone according to Examples 1 and 2.
Figure 7:
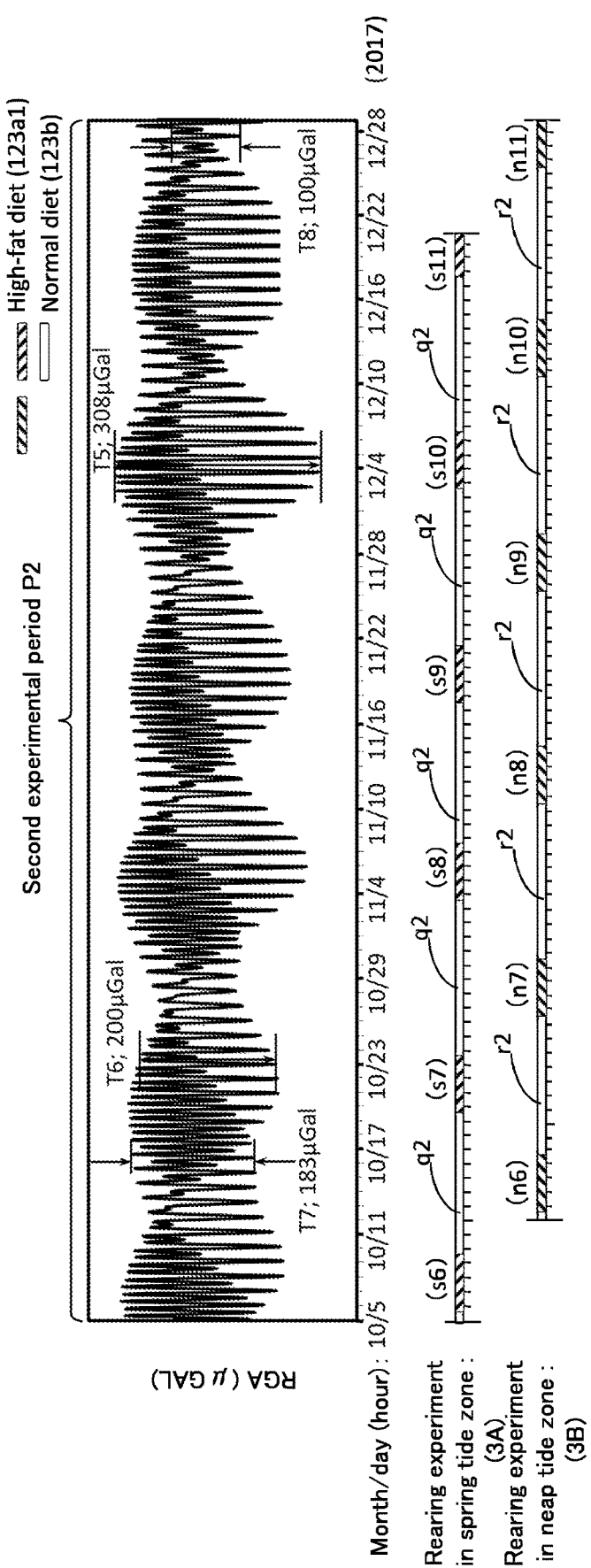
FIG. 7 is a view for explaining rearing experiments in a spring tide zone and a neap tide zone according to Example 3.
Figure 8:
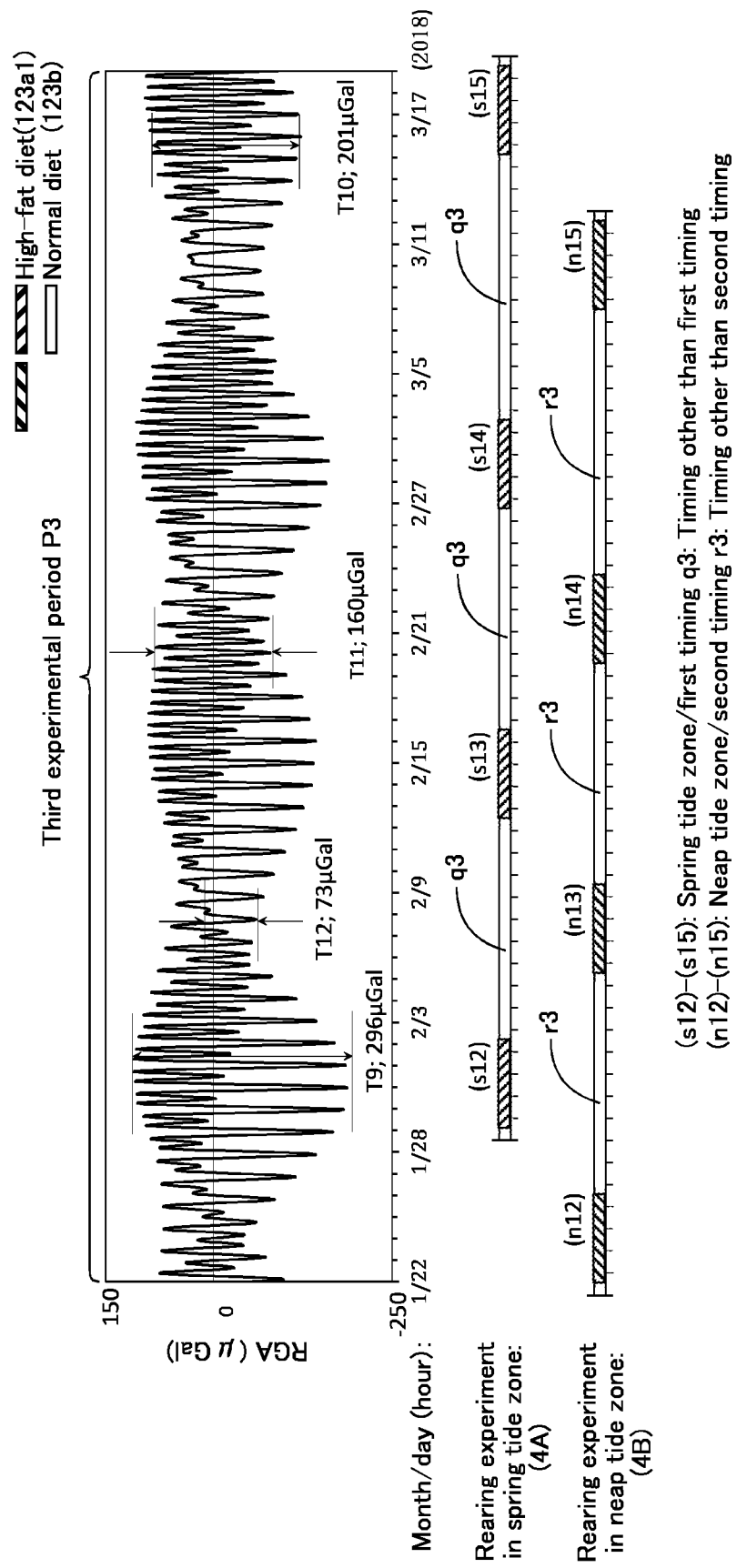
FIG. 8 is a view for explaining rearing experiments in a spring tide zone and a neap tide zone according to Example 4.

An apparatus for rearing an animal according to the present invention is an apparatus (1) for rearing an animal, which controls an increase in body weight or fat, the apparatus, as shown in FIG. 4, comprising: a food feeding means 12 for feeding, to the animal, on foods (123a, 123b) varying in fat component content according to the variation level (T1 to T12) of a tide-generating force (see FIGS. 6 to 8).

The apparatus (1) for rearing an animal according to the present invention is an apparatus suitable for implementing the method for rearing an animal according to the present invention. Descriptions overlapping with those concerning the method for rearing an animal described above will be omitted as much as possible, and the apparatus (I) for rearing an animal according to the present embodiment will be described below.

1. Tide-Generating Force Grasping Means

The variation level of the tide-generating force can be grasped using the tide-generating force grasping means 11. That is, the apparatus 1 for rearing an animal is provided with a tide-generating force grasping means 11 for grasping a tide-generating force in order to determine the variation level of the tide-generating force. Preferably, the tide-generating force grasping means 11 has a tidal information acquisition part 111 for preliminarily acquiring future tidal information periodically varying within a predetermined period. Furthermore, the tide-generating force grasping means 11 also has a tide-generating force variation value calculation part 112 for calculating (obtaining) the variation level of the tide-generating force within a unit period with reference to the tidal information acquired using the tidal information acquisition part 111.

As the tidal information acquisition part 111 of the tide-generating force grasping means 11, there can be utilized a device for calculating the relative gravity acceleration, a device for obtaining meteorological data (atmospheric pressure, tide name, tide level, tidal difference, etc.), a device for calculating or obtaining the ecliptic longitudinal difference (ecliptic longitudinal difference between the sun and the moon), a device for calculating the moon age calendar, and a device for calculating the distance from the center of the earth to the execution point. Among these pieces of tidal information, it is preferable to use information for predicting a periodical variation in (relative) gravity acceleration linked with a variation in solid tide and/or for the tide level linked with a variation in marine tide.

The tide-generating force variation value calculation part 112 of the tide-generating force grasping means 11 is preferably a device for determining the variation level of the tide-generating force from the information acquired by the tidal information acquisition part 111, which is a variation in tide-generating force grasped by utilizing an obtained or calculated value of at least one of the relative gravity acceleration, the distance from the center of the earth to the execution point, the tide name, the ecliptic longitudinal difference and the age of the moon.

When the apparatus 1 for rearing an animal is provided with the tide-generating force grasping means 11 described above, the level of the tide-generating force to be grasped periodically varies and thus the animal can be fed on foods at appropriate timings according to the cycle. It is preferable in that the future timings for feeding the animal on foods varying in fat ingredient content can be easily determined as planned.

2. Specific Timing Extraction Part

The apparatus 1 for rearing an animal may also be provided with a specific timing extraction part 13 for extracting a first timing showing a relatively large variation value of the tide-generating force or may be provided with a specific timing extraction part 13 for extracting a second timing showing a relatively small variation value of the tide-generating force, from within the above-mentioned predetermined period which is the whole period for rearing the animal. That is, the specific timing extraction part 13 may be any device that extracts at least one of the first timing and the second timing.

Specifically, the specific timing extraction part 13 refers to, for example, the variation value of the relative gravity acceleration (variation level of the tide-generating force) within the unit period calculated by the tide-generating force variation value calculation part 112 to perform processing for specifying a timing at which the variation value of the relative gravity acceleration (variation level of the tide-generating force) is relatively large. There is no particular limitation on the method for extracting a timing at which the above variation value is relatively large from within the predetermined period during which the tidal information has been acquired, and the specific timing extraction part 13 may be a device that extracts the specified timing as the first timing, or may be a device that extracts an appropriate group of timings including the specified timing as the first timing. Alternatively, similarly to the above, the specific timing extraction part 13 may be a device that specifies a timing at which the variation value of the relative gravity acceleration (the variation level of the tide-generating force) is relatively small, and extracts a timing at which the other tidal information overlaps with the specified timing as the second timing. As the "other tidal information", appropriate information similar to that described for the tidal information acquisition part 111 can be used.

When the apparatus 1 for rearing an animal is provided with the specific timing extraction part 13, it is possible to rear an animal which shows a more reliable change in degree of increase in body weight thereof or quantity of fat accumulated in the body thereof between at the first timing and at a timing other than the first timing or between at the second timing and at a timing other than the second timing.

3. Food Feeding Means

The food feeding means 12 is not particularly limited, and any device may be employed so long as it is suitable for feeding, to the animal, foods varying in fat ingredient content according to the variation level of the tide-generating force (for example, prediction data obtained by the tide-generating force grasping means 11).

Preferably, the food feeding means 12 has a food feeding part for feeding, at the first timing extracted by the specific timing extraction part 13, a food having a fat ingredient content relatively higher than at the timing other than the first timing. The food feeding means 12 may also have a food feeding part for feeding, at the second timing extracted by the specific timing extraction part 13, a food having a fat ingredient content relatively higher than that at the timing other than the second timing.

The food feeding means 12 is preferably, for example, [1] a device for feeding a food having a relatively high fat ingredient content to the animal at the first timing with a relatively high variation level of the tide-generating force (for example, at a timing of a spring tide) based on the prediction data on the tide-generating force grasped by the tide-generating force grasping means. Alternatively, the food feeding means 12 is preferably [2] a device for feeding a food having a relatively high fat ingredient content to the animal at the second timing with a relatively low variation level of the tide-generating force (for example, at a timing of a neap tide) based on the prediction data on the tide-generating force grasped by the tide-generating force grasping means.

EXAMPLES

Hereinafter, the present invention will be described in more detail by way of examples.

As the animal according to the present invention, a mouse (C57BL/6J) was used in this example to conduct rearing experiments involving feeding a high-fat diet having a relatively high fat ingredient content and a normal diet having a relatively low fat ingredient content according to the variation level of a tide-generating force. The results of the rearing experiments conducted using an apparatus for rearing an animal which will be described below within a predetermined period at a predetermined experimental place will be described.

[1] Apparatus for Rearing Animal

As shown in FIG. 4, the apparatus 1 for rearing an animal of the example is provided with a tide-generating force grasping means 11 for grasping the variation level of the tide-generating force, and a food feeding means 12 for feeding, to a mouse 2, foods 123 (high-fat diet 123*a*, normal diet 123*b*) varying in fat ingredient content.

The tide-generating force grasping means 11 is a device for grasping the tide-generating force within a predetermined period during which the animal is scheduled to be reared, and includes a tidal information acquisition part 111 for preliminarily acquiring periodically varying future tidal information and a tide-generating force variation value calculation part 112 for calculating the variation level of the tide-generating force within a unit period with reference to the tidal information.

The apparatus 1 for rearing an animal is further provided with a specific timing extraction part 13 that extracts a first timing showing a relatively large variation value of the tide-generating force from within the predetermined period during which the tide-generating force has been acquired by using the tidal information acquisition part 111, and can also extract a second timing showing a relatively small variation value thereof.

Tide-Generating Force Grasping Means

Specifically, the tide prediction system "GOTIC2" (http://www.miz.nao.acjp/staffs/nao99/) was used as the tide-generating force grasping means 11. The tide prediction system "GOTIC2" is a system which inputs the latitude and longitude of an execution site (Nagoya, Aichi) to grasp the change with time of the relative value of gravity acceleration [relative gravity acceleration (RGA)] within a predetermined period at the experimental place, thereby functioning as the tidal information acquisition part 111 that calculates future tidal information. Further, the tide prediction system "GOTIC2" is a system which functions also as the tide-generating force variation value calculation part 112 that calculates the variation level (variation value) of the tide-generating force for each cycle as a unit period with reference to the tidal information acquired by the tidal information acquisition part 111.

Specific Timing Extraction Part

The specific timing extraction part 13 is a system which specifies a relatively large variation value from among the variation values calculated by the tide-generating force variation value calculation part 112 and extracts a first timing at which a timing indicating the large variation value overlaps with a timing of a spring tide based on meteorological data. That is, the specific timing extraction part 13 extracted 4 days (hereinafter referred to also as "spring tide zone") as a timing of a spring tide with a large variation in tide-generating force, within the predetermined period during which the animal was scheduled to be reared. Also, the specific timing extraction part 13 is a system which specifies a relatively small variation value from among the variation values calculated by the tide-generating force variation value calculation part 112 and extracts a second timing at which a timing indicating the small variation value overlaps with a timing of a neap tide based on meteorological data. That is, the specific timing extracting part 13 extracted 4 days (hereinafter referred to also as "neap tide zone") as a timing of a neap tide with a small variation in tide-generating force, within the predetermined period during which the animal was scheduled to be reared.

For example, in Example 1 which will be described later, the spring tide zone and the neap tide zone were each extracted five times within the predetermined period for rearing the animal (see (s1) to (s5) and (n1) to (n5) in FIG. 6).

Food Feeding Means

The food feeding means 12 is a device provided with a food feeding part for feeding, to the mice 2, a high-fat diet 123a and a normal diet 123b varying in fat ingredient content, according to the variation level of the tide-generating force to be grasped, i.e., at the first timing extracted by the specific timing extraction part 13 and at a timing other than the first timing, respectively. The food feeding means 12 is also a device provided with a food feeding part for feeding, to the mice 2, the high-fat diet 123a and the normal diet 123b varying in fat ingredient content, at the second timing and at a timing other than the second timing, respectively.

The food feeding means 12 is configured so that the mouse 2 accommodated in a cage 121 can freely take the foods 123 charged into and held in a food holding part 122 as the food feeding part. The foods 123 include two kinds of foods, i.e., a normal diet 123b and a high-fat diet 123a having a fat ingredient content higher than that of the normal diet 123b. Either the normal diet 123b or the high-fat diet 123a was charged into and held in the food holding part 122 according to the variation level of the tide-generating force. Specifically, a device used as the food feeding means 12 was configured to charge the high-fat diet 123a into the food holding part 122 at the timings of the spring tide zone grasped by the tide-generating force grasping means 11 and to charge the normal diet 123b into the food holding part 122 at a timing other than the spring tide zone. Or, similarly, the device was configured to charge the high-fat diet 123a into the food holding part 122 at the timings of the neap tide zone and to charge the normal diet 123b into the food holding part 122 at a timing other than the neap tide zone.

In the present example, the foods 123 were charged into the food holding part 122 manually by humans, but can be automatically charged. For example, the apparatus 1 may be configured so that the food feeding means 12 is connected to the tide-generating force grasping means 11 or the specific timing extraction part 13 via a control part (not shown) to automatically charge an appropriate food 123 (high-fat diet 123a or normal diet 123b) depending on whether the spring tide zone or neap tide zone, or any other timing.

[2] Rearing of Animal

The above-described rearing apparatus 1 was used to conduct rearing experiments involving feeding foods which will be described later to the mouse 2 as will be described below.

Example 1

In Example 1, the period when the rearing experiments were carried out at the above experimental place was a predetermined first experimental period P1 [0040].

Figure 5:
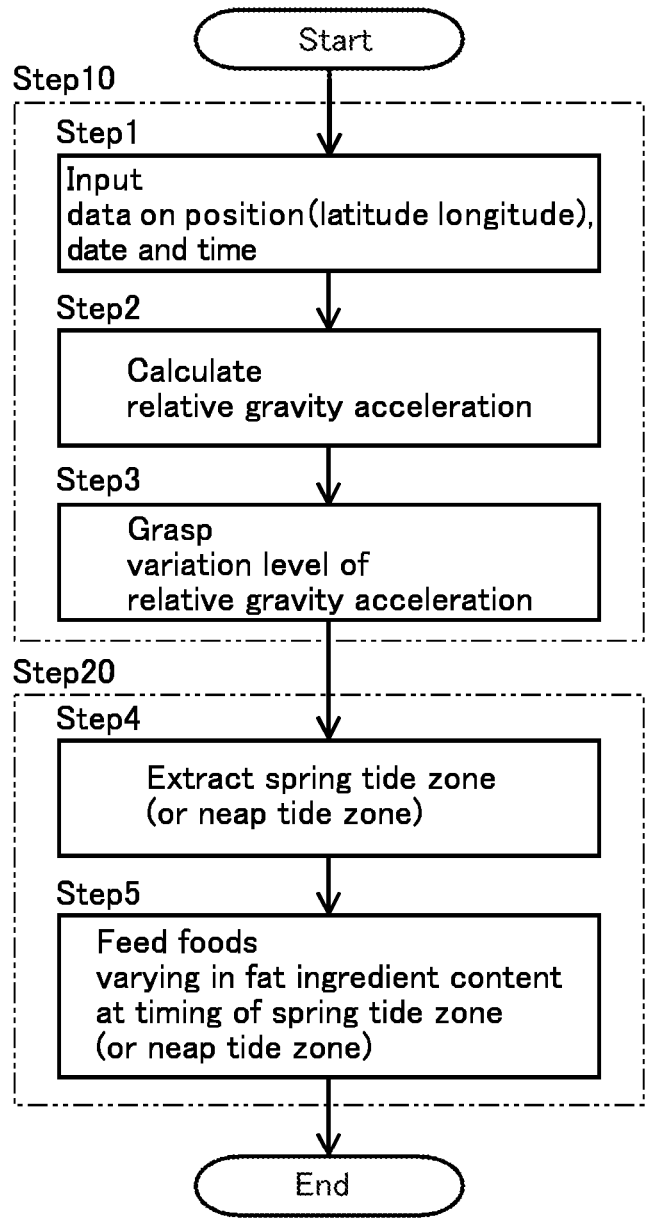
FIG. 5 is a flowchart for explaining a method for rearing an animal according to an Example.

First, as shown in FIG. 5, various pieces of data on information on the position (latitude and longitude) serving as the execution site where the rearing apparatus 1 was arranged and the above date and time of the first experimental period P1 were input into the above tide prediction system (tidal information acquisition part 111) of the tide-generating force grasping means 11 (Step 1). The above tide prediction system (tidal information acquisition part 111) of the tide-generating force grasping means 11 calculated the relative gravity acceleration at a predetermined time and its change over time using the tide-generating force prediction program "GOTIC2" by inputting each data (Step 2). Based on the change with time of the relative gravity acceleration grasped by calculation, the tide-generating force variation value calculation part 112 of the tide prediction system was used to calculate the variation level (tide-generating force variation value) of the acceleration between predetermined times (Step 3). Further, with reference to the obtained and grasped variation level of the acceleration and the meteorological data of tide name, the specific timing extraction part 13 was used to extract a timing of a spring tide zone with a high variation level of the acceleration (tide-generating force variation value) or a neap tide zone with a low variation level thereof within the first experimental period P1 (Step 4). Then, the food feeding means 12 was used to feed the foods 123 varying in fat ingredient content to the mouse 2 depending on whether the timings of the spring tide zone (or the neap tide zone) or other timings than the spring tide zone (or the neap tide zone) (Step 5). Specifically, a rearing experiment 1A in the spring tide zone was conducted in which, only at the timings of the spring tide zone, the mouse 2 was fed on the high-fat diet 123a having a fat ingredient content higher than that at a timing other than the spring tide zone. Likewise, a rearing experiment 1B in the neap tide zone was conducted in which, only at the timings of the neap tide zone, the mouse 2 was fed on the high-fat diet 123a having a fat ingredient content higher than that at a timing other than the neap tide zone.

1A. Rearing Experiment in Spring Tide Zone

Within the first experimental period P1, a rearing experiment 1A in a spring tide zone, involving feeding a high-fat diet only at a timing of the spring tide zone was conducted.

1. Spring Tide Zone

At the above experimental place, the spring tide zone was extracted as five timings (s1) to (s5), in total, within the first experimental period P1 as shown in FIG. 6. Specifically, within a period of about two months from May 25, 2017 to Aug. 2, 2017, the spring tide zones were extracted as (s1) May 25 to 29, (s2) June 8 to 12, (s3) June 23 to 27, (s4) July 7 to 11, and (s5) July 21 to 25, each of which was for about 4 days.

At the respective timings (s1) to (s5) of the spring tide zone, the variation level of a tide-generating force, that is, the variation level obtained from the relative gravity acceleration grasped by the tide-generating force grasping means 11 (tidal information acquisition part 111, tide-generating force variation value calculation part 112) was 262 μGal on average (the maximum variation level T1: 310 μGal; the minimum variation level T2: 221 μGal).

2. Mouse

In the rearing experiment in the spring tide zone, prepared were 4 mice (male) which were fed on a normal food before the beginning of the experiment and reared, and arrived at the age of 7 weeks on the first day, May 25, of the rearing within the first experimental period P1. All of the mice were accommodated in the cage 121 of the rearing apparatus 1 and maintained in a state where they could freely take only the food 123 charged into and held in the food holding part 122. The mice were reared until they grew up to the age of 15 weeks on July 25 when feeding at the last timing (s5) of the spring tide zone was conducted.

3. Normal Diet and High-Fat Diet

High Fat Diet 32 (CLEA Japan, Inc.) was used as a high-fat diet 123a1 to be fed only at the timings of the spring tide zone, and CE-2 (CLEA Japan, Inc.) was used as the normal diet 123b to be fed at a timing other than the spring tide zone. A comparison between the diets in terms of nutritional ingredients and energy amount is shown in Table 1.

TABLE 1

| Nutritional ingredient | | High Fat Diet 32 | CE-2 |
| --- | --- | --- | --- |
| Moisture | Weight % | 6.2 | 8.9 |
| Crude protein | | 25.5 | 25.3 |
| Crude fat | | 32.0 | 4.4 |
| Crude fiber | | 2.9 | 4.9 |
| Crude ash content | | 4.0 | 6.8 |
| Soluble nitrogen-free substance | | 29.4 | 49.7 |
| Calorie | Kcal/100 g | 507.6 | 339.4 |

1B. Rearing Experiment in Neap Tide Zone

Within the first experimental period P1, a rearing experiment 1B in a neap tide zone, involving feeding a high-fat diet only at a timing of the neap tide zone was conducted. The rearing experiment in the neap tide zone will be described below, mainly focusing on the differences from the above "Rearing experiment in spring tide zone".

1. Neap Tide Zone

At the above experimental place, the neap tide zone was extracted as five timings, in total: (n1) June 1 to 5, (n2) June 16 to 20, (n3) June 30 to July 4, (n4) July 14 to 18, (n5) July 29 to August 2, within about 2 months of the first experimental period P1, as shown in FIG. 6, each of which was for about 4 days.

At the respective timings (n1) to (n5) of the neap tide zone, the variation level of a tide-generating force, that is, the variation level obtained from the relative gravity acceleration grasped by the tide-generating force grasping means 11 was 122 μGal on average (the maximum variation level T3: 182 μGal; the minimum variation level T4: 72 μGal (in the neap tide zone)).

2. Mouse

The same mice as those in the above "Rearing experiment in spring tide zone" were used in the same manner. In the rearing experiment in the neap tide zone, used were mice which arrived at the age of 7 weeks on the first day, June 1, of the rearing in the neap tide zone within the first experimental period P1. The mice arrived at the age of 15 weeks on August 2 when the feeding at the last timing (n5) of the neap tide zone was finished.

3. Normal Diet and High-Fat Diet

The same high-fat diet and normal diet as those in the above "Rearing experiment in spring tide zone" were used.

2. Rearing

1. Transition of Body Weight

In the rearing experiment 1A in the spring tide zone, within the first experimental period P1, the high-fat diet 123a1 was fed at the timings (s1) to (s5) of the spring tide zone, and the normal diet 123b was fed at timings q1 other than the timings of the spring tide zone to rear the above mice. Through the first experimental period P1, feeding was continued so that either the high-fat diet 123a1 or the normal diet 123b would not be completely consumed, to an extent that the leftovers of the mice were always present. When the first day, May 25, of the rearing experiment in the spring tide zone was defined as Day "0", the body weights of all the mice were measured every 3 or 4 days until the last day, July 25, of the feeding at the last timing (s5) of the spring tide zone, which was 61 days after the first day, to determine the body weight average value (g) per mouse.

Also in the rearing experiment 1B in the neap tide zone, similarly as in the rearing experiment 1A in the spring tide zone, the feeding of the high-fat diet 123a1 was continued at the timings (n1) to (n5) of the neap tide zone, and the feeding of the normal diet 123b was continued at a timing r1 other than the respective timings of the neap tide zone. When the first day, June 1, of the rearing experiment in the neap tide zone was defined as Day "0", the body weight average value (g) was measured in the same manner as above until the last day, August 2, of the feeding at the last timing (n5) of the neap tide zone, which was 62 days after the first day.

Figure 9:
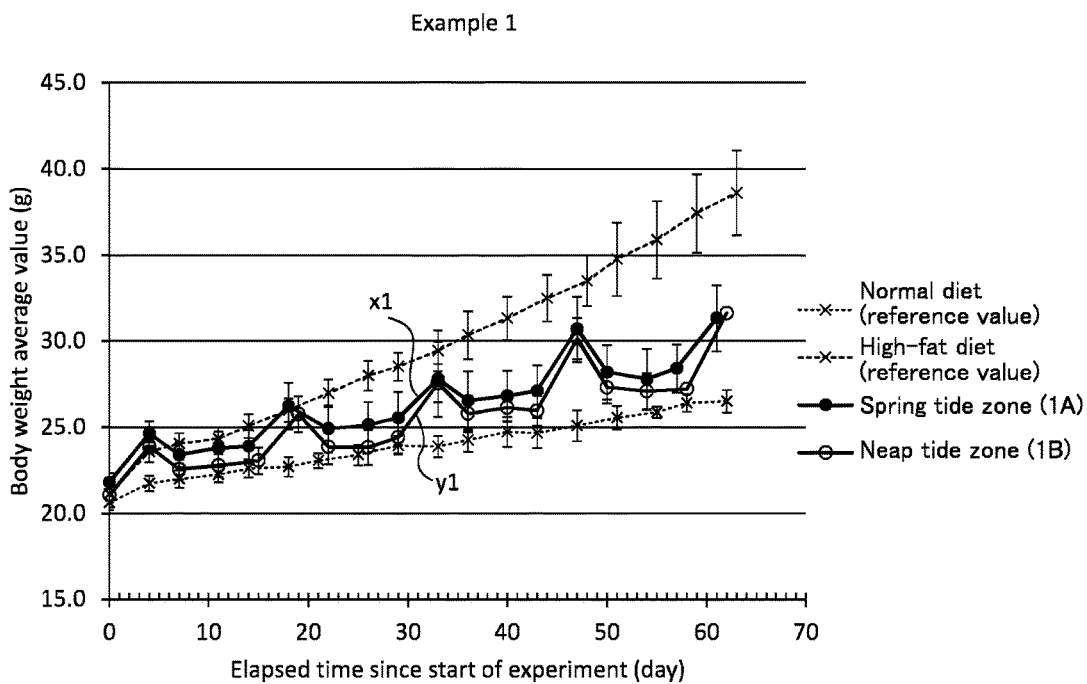
FIG. 9 is a graph showing the transition of the body weight average value of mice according to Example 1.

FIG. 9 shows a graph of the "spring tide zone (1A)" and "neap tide zone (1B)", respectively, in which the time from Day "0" to Day 61 or Day 62, as described above, is plotted on the horizontal axis and the obtained body weight average value is plotted on the longitudinal axis, for the rearing experiment 1A in the spring tide zone and the rearing experiment 1B in the neap tide zone.

2. Body Weight Increase Rate

For the rearing experiment 1A in the spring tide zone, the body weight increase rate increasing after feeding of the high-fat diet was calculated. The body weight increase rates at the timings of the spring tide zone were determined using the body weight average value [W1] before feeding of the high-fat diet and the body weight average value [W2] after feeding of the high-fat diet, among the body weight average values that changed as described above in accordance with the following equation 1. The body weight average value [W1] before feeding of the high-fat diet is a body weight average value measured during feeding of the normal diet immediately before the beginning of each of the timings (s1) to (s5) of the spring tide zone. The average body weight measurement value [W2] after feeding of the high-fat diet is a body weight average value on the last day of each of the timings (s1) to (s5) of the spring tide zone.

Also for the rearing experiment 1B in the neap tide zone, the body weight increase rates at the timings of the neap tide zone were calculated in accordance with the following equation 1, in the same manner as in the rearing experiment 1A in the spring tide zone.

$$\text{Body weight increase rate (\%)} = 100 \times ([W2]-[W1])/[W1]$$

According to Equation 1, the body weight increase rates at the five timings (s1) to (s5), in total, of the spring tide zone and at the five timings (n1) to (n5), in total, of the neap tide zone calculated for the rearing experiments in the spring tide and neap tide zone, respectively, are indicated in Table 3.

Figure 13:
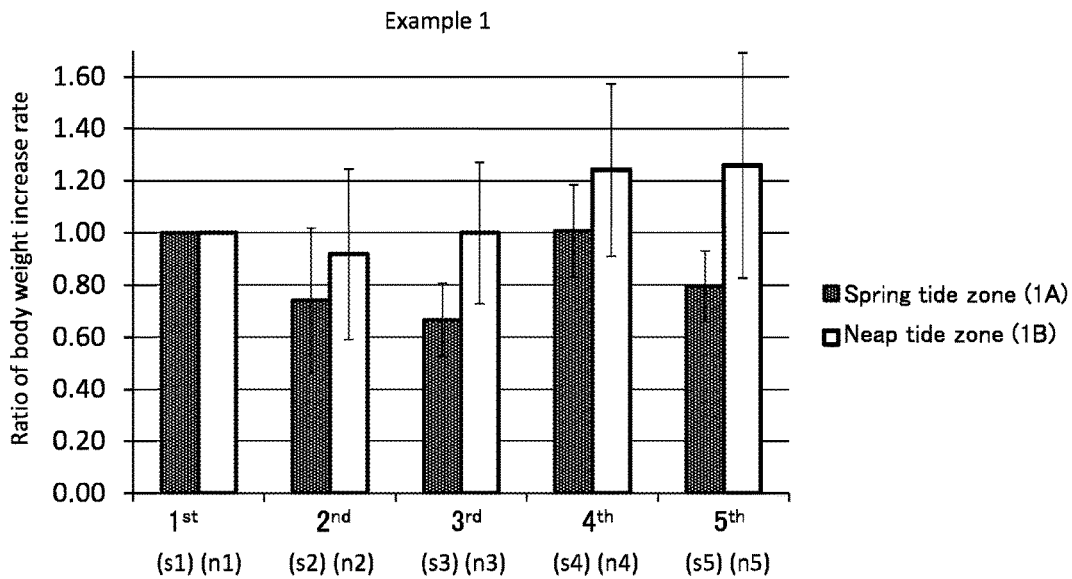
FIG. 13 is a graph showing the ratio of body weight increase rate of the mice according to Example 1.

Further, FIG. 13 shows a bar chart of the "spring tide zone (1A)", which indicates, when the body weight increase rate at the first timing (s1) of the spring tide zone is defined as "1", the body weight increase rates at the second to fifth timings (s2) to (s5) of the spring tide zone as the ratios thereof to the body weight increase rate at the first timing. Similarly, FIG. 13 shows a bar chart of the "neap tide zone (1B)", which indicates, when the body weight increase rate at the first timing (n1) of the neap tide zone is defined as "1", the body weight increase rates at the second to fifth timings (n2) to (n5) of the neap tide zone as the ratios thereof to the body weight increase rate at the first timing.

3. Fat Quantity Per Body Weight

Figure 17:
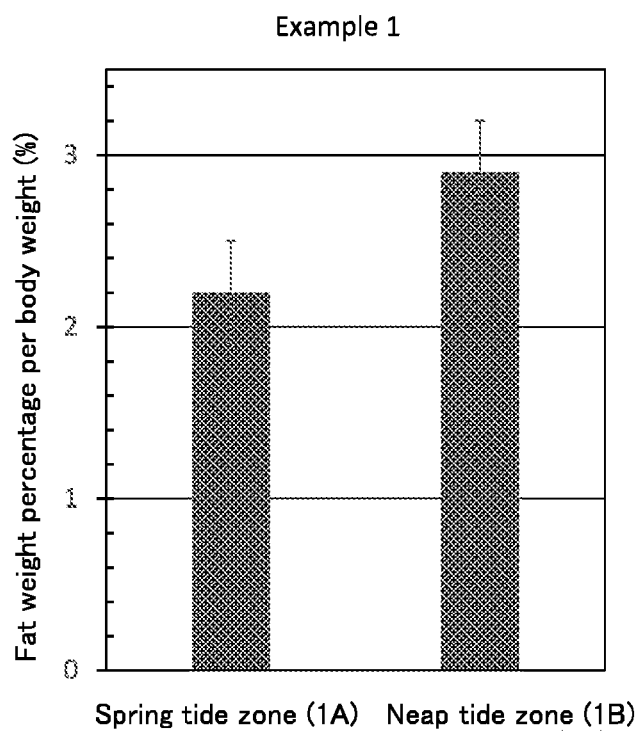
FIG. 17 is a graph showing the fat weight of the mice according to Example 1.

The body weights of all the mice which arrived at the age of 15 weeks after feeding at the last timing (s5) of the spring tide zone were measured, and adipose tissues (visceral fat) around the epididymis were excised and respectively weighed. The body weight and adipose tissue weight were similarly measured for all the mice which arrived at the age of 15 weeks after feeding at the last timing (n5) of the neap tide zone. FIG. 17 shows a bar chart of the "spring tide zone (1A)" and "neap tide zone (1B)", respectively, which indicates the fat quantity (g) per 100 (g) of the body weight calculated from these measured values as a percentage (%).

Example 2

1. Rearing Experiments in Spring Tide Zone and Neap Tide Zone

In Example 2, conducted were rearing experiments different from those in Example 1 only in that HFD-60 (manufactured by Oriental Yeast Co. Ltd.) was used as a high-fat diet 123a2 to be fed to the mice at each of the above-mentioned timings (s1) to (s5) and (n1) to (n5) of the spring tide and neap tide zone. Specifically, as shown in FIG. 6, at the same experimental place and within the same first experimental period P1 as in Example 1, the rearing experiment 2A in the spring tide zone and the rearing experiment 2B in the neap tide zone were similarly conducted using the rearing apparatus 1. A comparison in composition of the ingredients between the high-fat diet 123a2 used in Example 2 and the above-indicated High Fat Diet 32 (CLEA Japan, Inc.) as the high-fat diet 123a1 used in Example 1 is shown in Table 2.

TABLE 2

| Composition of ingredients | HFD-60 (wt %) | High Fat Diet 32 (wt %) |
|---|---|---|
| Casein | 25.90 | |
| Milk casein | | 24.50 |
| Egg white powder | | 5.00 |
| Beef tallow | 32.87 | |
| Powdered beef tallow (containing 80% beef tallow) | | 15.88 |
| Soybean oil | 1.99 | |
| Safflower oil (high oleic acid type) | | 20.00 |
| α corn starch | 15.94 | — |
| Sucrose | 5.48 | 6.75 |
| Lactose | — | 6.93 |
| Vegetable fiber | 6.58 | |
| Crystalline cellulose | | 5.50 |
| AIN-93M mineral mix | 3.49 | |
| AIN 93G mineral mix | | 5.00 |
| AIN-93M Vitamin mix | 1.00 | |
| AIN 93 vitamin mix | | 1.40 |
| L-cystine | 0.36 | 0.43 |
| Choline bitartrate | 0.25 | 0.36 |
| Tertiary butyl hydroquinone | 0.00 | 0.00 |
| Multidextrin | 5.98 | 8.25 |
| Calcium carbonate | 0.18 | — |

2. Rearing

1. Transition of Body Weight

Figure 10:
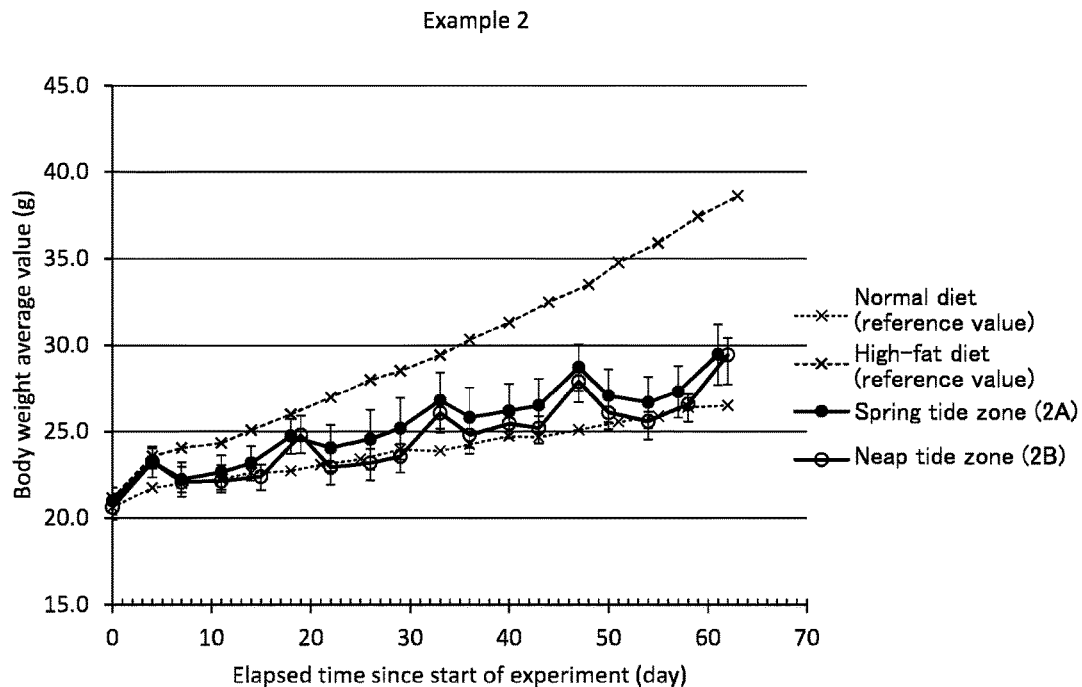
FIG. 10 is a graph showing the transition of the body weight average value of mice according to Example 2.

FIG. 10 shows a graph of the "spring tide zone (2A)" and "neap tide zone (2B)", respectively, in which the time from Day "0" to Day 61 or Day 62, as described above, is plotted on the horizontal axis and the obtained body weight average value is plotted on the longitudinal axis, for the rearing experiment 2A in the spring tide zone and the rearing experiment 2B in the neap tide zone in Example 2 which were conducted in the same manner as in Example 1.

2. Body Weight Increase Rate

Table 3 shows the body weight increase rates calculated for the rearing experiments 2A and 2B in the spring tide zone and the neap tide zone, respectively, of Example 2 in accordance with the above equation 1, as in Example 1.

Figure 14:
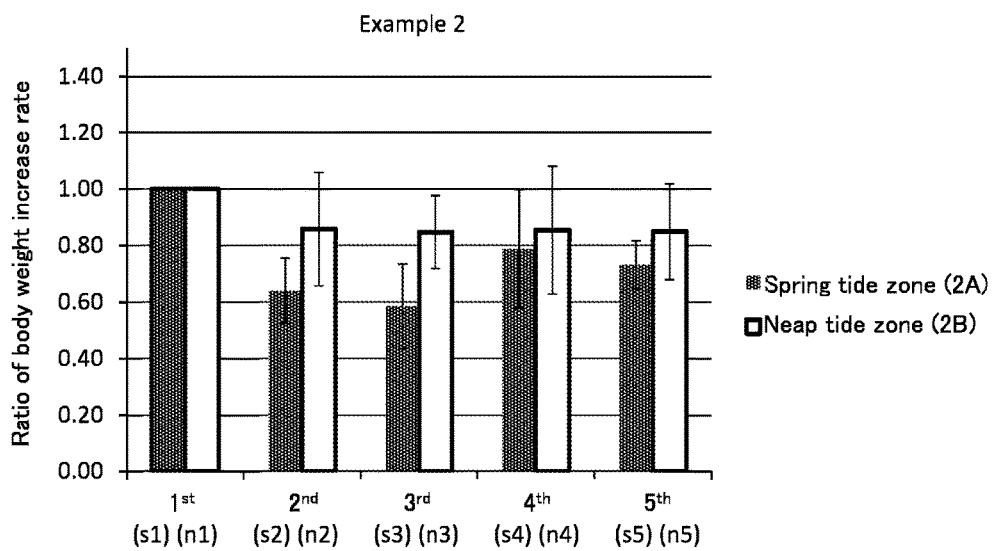
FIG. 14 is a graph showing the ratio of body weight increase rate of the mice according to Example 2.

In addition, FIG. 14 shows a bar chart of the "spring tide zone (2A)" and "neap tide zone (2B)", respectively, which indicates, when the body weight increase rates for the first timings (s1) and (n1) of the spring tide and neap tide zone, respectively, are each defined as "I", the body weight increase rates at the respective second to fifth timings (s2), (n2) to (s5), (n5) thereof as the ratios thereof to the body weight increase rate at the first timing.

3. Fat Quantity Per Body Weight

Figure 18:
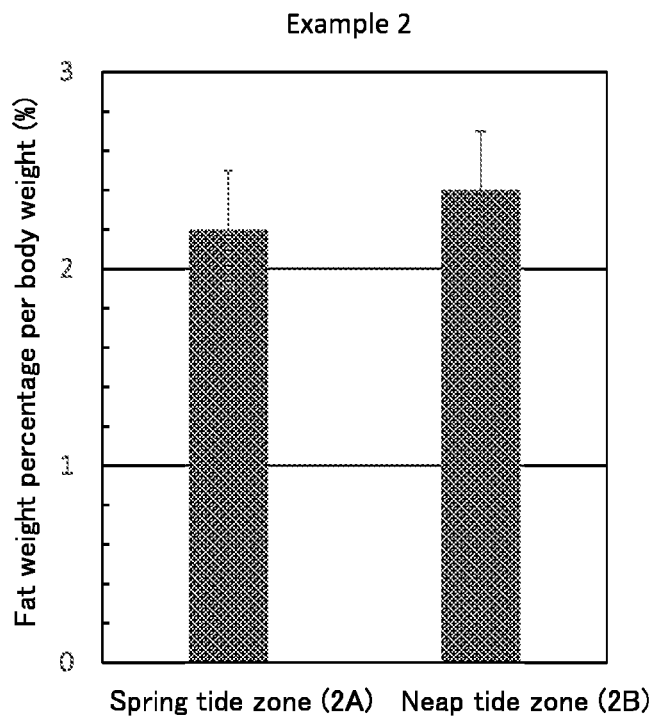
FIG. 18 is a graph showing the fat weight of the mice according to Example 2.

FIG. 18 shows a bar chart of the "spring tide zone (2A)" and "neap tide zone (2B)", respectively, which indicates the percentage (%) of the fat quantity (g) per 100 (g) of the body weight of the mice which arrived at the age of 15 weeks after feeding at the last timing (s5) of the spring tide zone and the mice which arrived at the age of 15 weeks after feeding at the last timing (n5) of the neap tide zone in the same manner as in Example 1 for the rearing experiments in the spring tide and neap tide zone of Example 2.

Example 3

1. Rearing Experiments in Spring Tide Zone and Neap Tide Zone

In Example 3, conducted were rearing experiments different from those in Example 1 only in that the predetermined periods when the rearing experiments were conducted fell within the second experiment period P2. Specifically, under the condition that the same experimental place, mice, foods and rearing apparatus 1 as those in Example 1 were used, a rearing experiment 3A in the spring tide zone and a rearing experiment 3B in the neap tide zone were similarly conducted. The second experiment period P2 was for about two and a half months, from Oct. 5, 2017 to Dec. 28, 2017.

1. Spring Tide Zone

At the above experimental place, the spring tide zone was extracted as six timings, in total: (s6) October 5 to 9, (s7) October 19 to 23, (s8) November 3 to 7, (s9) November 17 to 21, (s10) December 2 to 6, and (s11) December 17 to 20, within about two and a half months from October 4 to Dec. 28, 2017 of the experimental period P2, as shown in FIG. 7, each of which was for about 4 days (only s11 was for 3 days). In addition, in FIG. 7, symbol q2 represents a timing other than the spring tide zone.

At the respective timings (s6) to (s11) of the spring tide zone, the variation level of a tide-generating force, that is, the variation level obtained from the relative gravity acceleration grasped by the tide-generating force grasping means 11 was 246 μGal on average (T5: the maximum variation level, 308 μGal; T6: the minimum variation level, 200 μGal).

2. Neap Tide Zone

At the above experimental place, similarly, the neap tide zone was extracted as six timings, in total: (n6) October 12 to 16, (n7) October 26 to 30, (n8) November 10 to 14, (n9) November 25 to 29, (n10) December 10 to 14, and (n11) December 25 to 28 within the second experimental period P2, as shown in FIG. 7, each of which was for about 4 days (only n11 was for 3 days). In addition, in FIG. 7, symbol r2 represents a timing other than the neap tide zone.

At the respective timings (n6) to (n11) of the neap tide zone, the variation level of a tide-generating force, that is, the variation level obtained from the relative gravity acceleration grasped by the tide-generating force grasping means 11 was 140 μGal on average (T7: the maximum variation level, 183 μGal; T8: the minimum variation level, 100 μGal).

2. Rearing

1. Transition of Body Weight

Within the second experimental period P2, the body weight average values (g) of all the mice were measured in the same manner as in Example 1, until the last day, December 20, of the feeding at the last timing (S11) of the spring tide zone, which was 76 days after the first day (defined as Day "0"), October 5, of the rearing experiment 3A in the spring tide zone and until the last day, December 28, of the feeding at the last timing (n11) of the neap tide zone, which was 77 days after the first day (defined as Day "0"), October 12, of the rearing experiment 3B in the neap tide zone.

Figure 11:
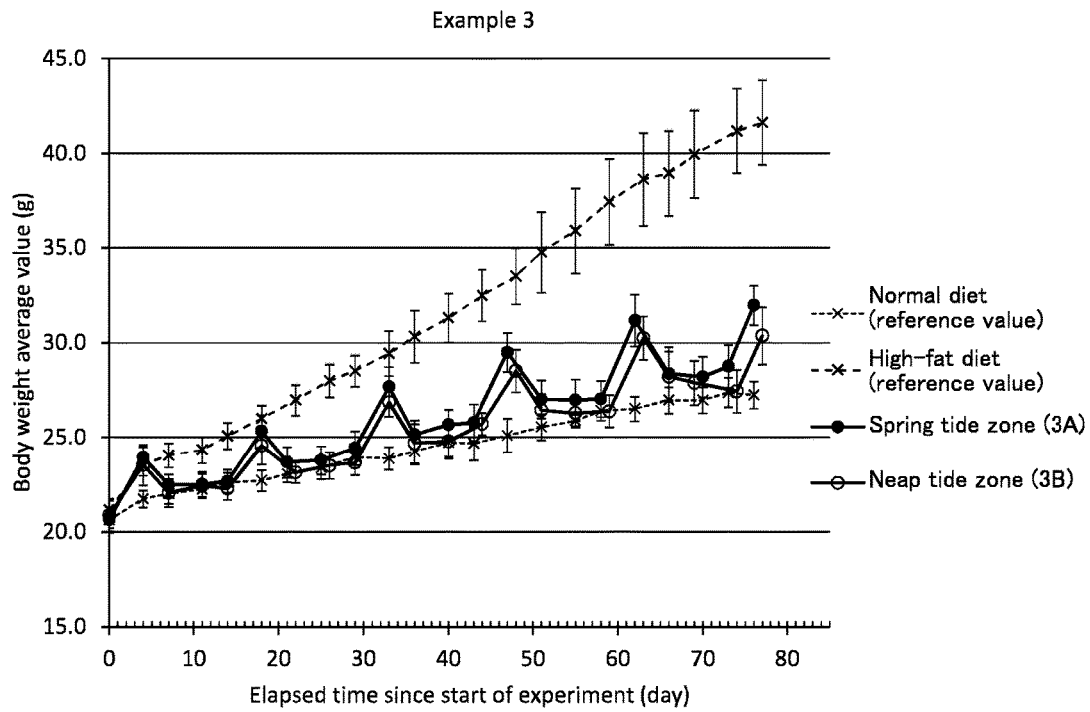
FIG. 11 is a graph showing the transition of the body weight average value of mice according to Example 3.

FIG. 11 shows a graph of the "spring tide zone (3A)" and "neap tide zone (3B)", respectively, in which the time from Day "0" to Day 76 or Day 77, as described above, is plotted on the horizontal axis and the obtained body weight average value is plotted on the longitudinal axis, for the rearing experiment 3A in the spring tide zone and the rearing experiment 3B in the neap tide zone in Example 3.

2. Body Weight Increase Rate

The following table 3 shows the body weight increase rates calculated for the rearing experiments 3A and 3B in the spring tide zone and the neap tide zone, respectively, of Example 3 in accordance with the above equation 1, as in Example 1.

Figure 15:
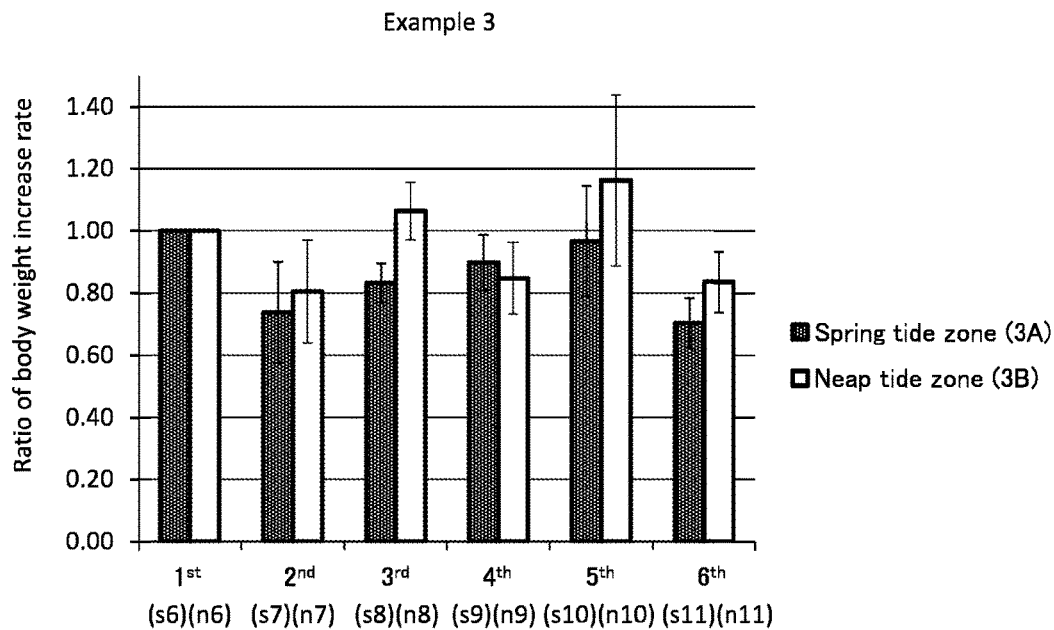
FIG. 15 is a graph showing the ratio of body weight increase rate of the mice according to Example 3.

In addition, FIG. 15 shows a bar chart of the "spring tide zone (3A)" and "neap tide zone (3B)", respectively, which indicates, when the body weight increase rates for the first timings (s6) and (n6) of the spring tide and neap tide zone, respectively, are each defined as "1", the body weight increase rates at the respective second to sixth timings (s7), (n7) to (s11), (n11) thereof, as the ratios thereof to the body weight increase rate at the first timing.

Example 4

1. Rearing Experiments in Spring Tide Zone and Neap Tide Zone

In Example 4, conducted were rearing experiments different from those in Example only in that the predetermined periods when the rearing experiments were conducted fell within the third experiment period P3. Specifically, under the condition that the same experimental place, mice, foods, and rearing apparatus 1 as those in Example 1 were used, a rearing experiment 4A in the spring tide zone and a rearing experiment 4B in the neap tide zone were similarly conducted. The third experiment period P3 was for about two months, from Jan. 22, 2018 to Mar. 18, 2018.

1. Spring Tide Zone

At the above experimental place, the spring tide zone was extracted as four timings, in total: (s12) January 29 to February 2, (s13) February 12 to 16, (s14) February 26 to March 2, and (s15) March 14 to 18, within about two months, from Jan. 22, 2018 to Mar. 18, 2018, of the third experimental period P3, as shown in FIG. 8, each of which was for about 4 days. In FIG. 8, symbol q3 represents a timing other than the spring tide zone.

At the respective timings (s12) to (s15) of the spring tide zone, the variation level of a tide-generating force, that is, the variation level obtained from the relative gravity acceleration grasped by the tide-generating force grasping means 11 was 243 μGal on average (T9: the maximum variation level, 296 μGal; T10: the minimum variation level, 20 μGal).

2. Neap Tide Zone

At the above experimental place, the neap tide zone was similarly extracted as four timings, in total: (n12) January 22 to 26, (n13) February 5 to 9, (n14) February 19 to 23, and (n15) March 7 to 11, within the third experimental period P3, as shown in FIG. 8, each of which was for about 4 days. In addition, in FIG. 8, symbol r3 represents a timing other than the neap tide zone.

At the respective timings (n12) to (n15) of the neap tide zone, the variation level of a tide-generating force, that is, the variation level obtained from the relative gravity acceleration grasped by the tide-generating force grasping means 11 was 109 μGal on average (T11: the maximum variation level, 160 μGal; T12: the minimum variation level, 73 μGal).

2. Rearing

1. Transition of Body Weight

Within the third experimental period P3, the body weight average values (g) of all the mice were measured in the same manner as in Example 1, until the last day, March 18 of the feeding at the last timing (s15) of the spring tide zone, which was 48 days after the first day (defined as Day "0"), January 29, of the rearing experiment 4A in the spring tide zone and until the last day, March 11, of the feeding at the last timing (n11) of the neap tide zone, which was 48 days after the first day (defined as Day "0"), Jan. 22, 2018 of the rearing experiment 4B in the neap tide zone.

Figure 12:
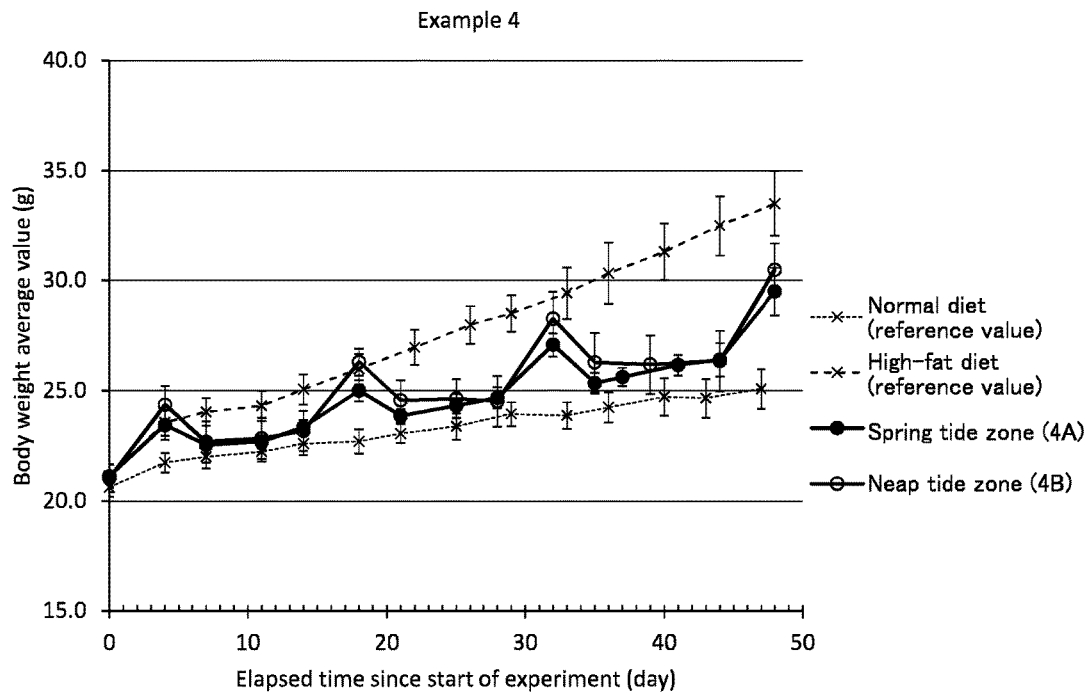
FIG. 12 is a graph showing the transition of the body weight average value of mice according to Example 4.

FIG. 12 shows a graph of the "spring tide zone (4A)" and "neap tide zone (4B)", respectively, in which the time from Day "0" to Day 48, as described above, is plotted on the horizontal axis and the obtained body weight average value is plotted on the longitudinal axis, for the rearing experiment 4A in the spring tide zone and the rearing experiment 4B in the neap tide zone of Example 4.

2. Body Weight Increase Rate

The following table 3 shows the body weight increase rates calculated for the rearing experiments 4A and 4B in the spring tide zone and the neap tide zone, respectively, of Example 4 in accordance with the above equation 1, as in Example 1.

Figure 16:
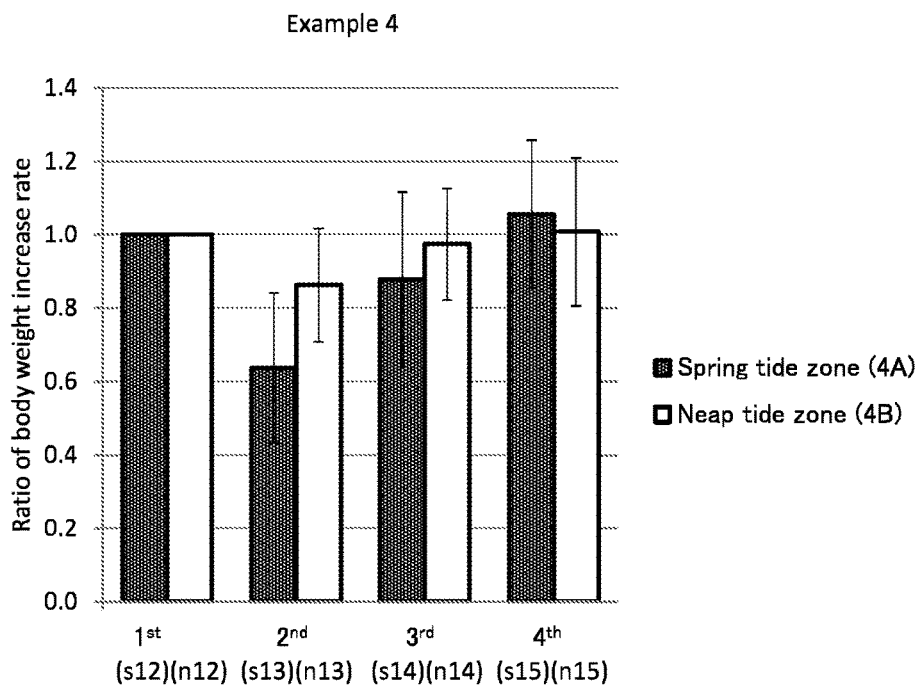
FIG. 16 is a graph showing the ratio of body weight increase rate of the mice according to Example 4.

In addition, FIG. 16 shows a bar chart of the "spring tide zone (4A)" and "neap tide zone (4B)", respectively, which indicates, when the body weight increase rates for the first timings (s12) and (n12) of the spring tide zone and neap tide zone, respectively, are each defined as "I", the body weight increase rates at the respective second to fourth timings (s13), (n13) to (s15), (n15) thereof, as the ratios thereof to the body weight increase rate at the first timing.

3. Fat Quantity Per Body Weight

Regarding the rearing experiments of the spring tide zone and the neap tide zone in Example 4, in the same manner as in Example 1, the body weights of all the mice which were subjected to feeding at the last timing (s15) of the spring tide zone and arrived at the age of 13 weeks on the next day were measured, and adipose tissues (visceral fat) around the epididymis were excised and respectively weighed. Similarly, the body weights of the mice which were subjected to feeding at the last timing (n15) of the neap tide zone and arrived at the age of 13 weeks on the next day were measured, and the weight of the adipose tissues were weighed.

Figure 19:
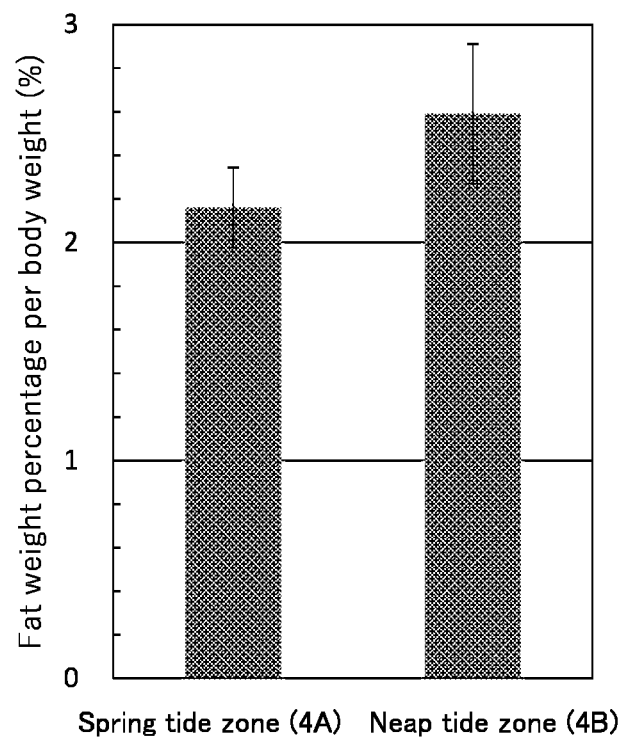
FIG. 19 is a graph showing the fat weight of the mice according to Example 4.

FIG. 19 shows a bar chart of the "spring tide zone (4A)" and "neap tide zone (4B)", respectively, which indicates the fat quantity (g) per 100 (g) of the body weight calculated from these measured values as a percentage (%).

transition in the rearing experiment 1B in the neap tide zone according to Example 1, the gradient of the graph at the timings when the body weight is steadily increasing is slightly greater for the rearing experiment 1B in the neap tide zone (See x1 and y1 of FIG. 9). So, it can be seen that the rate of increase in body weight is higher when switching from the normal diet to the high-fat diet at the timings of the neap tide zone than when similarly switching at the timings of the spring tide zone. Similarly in the rearing experiments 2A and 2B, rearing experiments 3A and 3B, and rearing experiments 4A and 4B of Examples 2 to 4, respectively, there is a tendency that the rate of increase in body weight is higher when switching from the normal diet to the high-fat diet at the timings of the neap tide zone than when switching at the timings of the spring tide zone.

FIGS. 13 to 16 are graphs showing the rate of increase in body weight (body weight increase rate (%)) at the respective timings of the spring tide zone or the neap tide zone indicated in Table 3 for the rearing experiments 1A to 4A and 1B to 4B in the spring tide zone and the neap tide zone according to Examples 1 to 4, respectively, as the "ratio" thereof to the rate of increase in body weight (body weight increase rate (%)) at the first timing of the spring tide zone or the neap tide zone.

As shown in FIG. 13, it can be seen that, when the rate of increase in body weight at the first timing (s1) of the spring zone or the first timing (n1) of the neap tide zone is defined as "1", the "ratios" corresponding to the second and subsequent timings (n2) to (n5) of the neap tide zone are higher than the "ratios" corresponding to the second and subsequent timings (s2) to (s5) of the spring tide zone. Similarly

TABLE 3

| | | | Body weight increase rate (%) | | | | | |
|---|---|---|---|---|---|---|---|---|
| | | | $1^{st}$ | $2^{nd}$ | $3^{rd}$ | $4^{th}$ | $5^{th}$ | $6^{th}$ |
| Example 1 | Spring tide zone 1A | (s1)-(s5) | 13.0 | 9.9 | 8.7 | 13.2 | 10.3 | — |
| | Neap tide zone 1B | (n1)-(n5) | 13.5 | 11.7 | 12.9 | 16.1 | 16.1 | |
| Example 2 | Spring tide zone 2A | (s1)-(s5) | 10.8 | 6.8 | 6.5 | 8.4 | 7.9 | — |
| | Neap tide zone 2B | (n1)-(n5) | 12.8 | 10.7 | 10.7 | 10.8 | 10.8 | |
| Example 3 | Spring tide zone 3A | (s6)-(s11) | 16.0 | 11.7 | 13.3 | 14.4 | 15.3 | 11.2 |
| | Neap tide zone 3B | (n6)-(n11) | 12.8 | 10.2 | 13.5 | 10.9 | 14.6 | 10.7 |
| Example 4 | Spring tide zone 4A | (s12)-(s15) | 11.0 | 7.1 | 9.8 | 11.8 | — | — |
| | Neap tide zone 4B | (n12)-(n15) | 15.8 | 13.5 | 15.3 | 15.8 | | |

[3] Evaluation of Animal Rearing

1. Body Weight Increase

As described above, FIGS. 9 to 12 are graphs showing transition of the body weight of the mice for the rearing experiments 1A to 4A and 1B to 4B in the spring tide and neap tide zone according to Examples 1 to 4, respectively. The dotted line in each graph shows the transition of the body weight of the mice in the case where only the high-fat diet 123a1, 123a2 or only the normal diet 123b is fed to rear the mice within the first to third experimental periods P1, P2 and P3.

From FIGS. 9 to 12, it can be understood that the body weight of the mice fed only on the high-fat diet or normal diet changes with a simple increase, whereas, in the rearing experiments 1A to 4A and 1B to 4B in the spring tide zone and the neap tide zone, respectively, the body weight increases upon switching from the normal diet to the high-fat diet, and the body weight decreases upon switching from the high-fat diet to the normal diet. Furthermore, in comparison between the body weight transition in the rearing experiment 1A in the spring tide zone and the body weight in FIG. 14, it can be seen that the "ratios" corresponding to the second and subsequent timings (n2) to (n5) of the neap tide zone are higher than the "ratios" corresponding to the second and subsequent timings (s2) to (s5) of the spring tide zone. Also in FIGS. 15 and 16, almost the same tendency is recognized.

From the above, it can be understood that the rate (degree) of increase in body weight of an animal changes by feeding, to the animal, foods varying in fat ingredient content according to the variation level of a tide-generating force.

It can be understood that, especially at a timing of a spring tide, the animal is fed on a high-fat food having the fat ingredient content higher than that at a timing other than the spring tide, thereby making it possible to suppress the degree of increase in body weight of the animal, although the animal is fed on the high-fat food, as compared with when similarly feeding the high-fat food at the timing of the neap tide.

From this result, for example, when it is intended to suppress the degree of increase in body weight, as will be described below, it is possible to effectively rear the animal according to expectation.

When it is desired to suppress a rapid increase in body weight of an animal while there is an expectation that a lot of predetermined preferable fat ingredients should be fed; and When it is desired to suppress a rapid increase in body weight of a pet while there is an expectation of promoting the growth of the pet.

In addition, it can be understood that, at a timing of a neap tide, the animal is fed on a high-fat food having the fat ingredient content higher than that at a timing other than the neap tide, thereby making it possible to increase the degree of increase in body weight of the animal, as compared with when similarly feeding the high-fat food at a timing of the spring tide.

From this result, for example, when it is intended to increase the degree of increase in body weight, as will be described below, it is possible to effectively rear the animal according to expectation.

When there is an expectation of health maintenance through moderate body fat maintenance, with the intention to increase the body weight through intake of a small amount of food.

2. Fat Increase

FIGS. 17 to 19 are graphs comparing the predetermined fat quantities per 100 g of the body weight of the mice at the end of the respective rearing experiments 1A, 2A and 4A in the spring tide zone and the respective rearing experiments 1A, 2A and 4A in the neap tide zone according to Examples 1, 2 and 4.

As shown in the figures, it is understood that, in Examples 1, 2 and 4, the mice subjected to the rearing experiments 1A, 2A and 4A in the spring tide zone have a fat quantity lower than that of the mice subjected to the rearing experiments 1B, 2B and 4B in the neap tide zone.

From the above, it can be seen that the quantity of fat accumulated in the body of an animal is changed by feeding, to the animal, to foods varying in fat ingredient content according to the variation level of the tide-generating force. That is, even if the same food is fed in the same way, the quantity of fat accumulated in the body of the animal can be changed by adjusting the feeding timing according to the variation level of the tide-generating force.

Especially, it can be understood that, at a timing of a spring tide, the animal is fed on a high-fat food having the fat ingredient content higher than that at a timing other than the spring tide, thereby making it possible to suppress the quantity of fat accumulated in the body of the animal, although the animal is fed on the high-fat food, as compared with when similarly feeding the high-fat food at a timing of the neap tide.

From this result, for example, when it is intended to suppress the fat quantity, as will be described below, it is possible to effectively rear the animal according to expectation.

When it is intended to suppress fat accumulation, thereby realizing animal welfare without inhibiting free behavior of an animal (livestock) and fattening the animal healthily.

In addition, it can be understood that, at a timing of a neap tide, the animal is fed on a high-fat food having the fat ingredient content higher than that at a timing other than the neap tide, thereby making it possible to increase the quantity of fat accumulated in the body of the animal, as compared with when similarly feeding the high-fat food at the timing of the spring tide.

From this result, for example, when it is intended to increase the quantity of fat accumulated in the body of the animal, as will be described below, it is possible to effectively rear an animal according to expectation.

When rearing livestock that improves taste by increasing the fat quantity.

As described above, the method and apparatus for rearing an animal according to the present invention make it possible to rear an animal as expected, with the intention of an expected degree of increase in body weight or fat quantity. Therefore, it is possible to improve the animal rearing efficiency, to shorten the rearing period, and to suppress the rearing cost in various fields including animal farming.

In addition, in the method for rearing an animal according to the present invention, the present rearing apparatus is used to predict a future variation in tide-generating force by utilizing the tide-generating force grasping means before starting the rearing of the animal. After preliminarily grasping the variation level of the tide-generating force and determining the timings for feeding foods varying in fat ingredient content, it is possible to rear the animal while feeding as usual. Therefore, it is unnecessary to provide a rearing apparatus which acquires actual information over a predetermined period for rearing the animal, thereby making it possible to eliminate inconvenience that the operation of the system becomes exaggerated as in the prior art. Or, the time and effort required to feed a predetermined pet food product twice a day according to a predetermined method are unnecessary, so that the daily burden for rearing the animal can be reduced.

What is claimed is:

1. A method for rearing an animal, which controls an increase in body weight or fat, the method comprising:
   grasping a tide-generating force; and
   feeding, to the animal, foods varying in fat ingredient content according to a variation level of the tide-generating force between at a first timing and at a timing other than the first timing, or between at a second timing and at a timing other than the second timing,
   wherein the first timing is a timing of a spring tide and, at the timing of the spring tide, the animal is fed a high-fat diet food having a higher fat ingredient content than a normal diet food, which is fed at a timing other than the spring tide, and
   wherein the second timing is a timing of a neap tide and, at the timing of the neap tide, the animal is fed the high-fat diet food having the higher fat ingredient content than the normal diet food, which is fed at a timing other than the neap tide.

2. The method for rearing an animal according to claim 1, wherein grasping the tide-generating force comprises:
   preliminarily acquiring future tidal information which, within a predetermined period, periodically varies; and
   determining the variation level of the tide-generating force within a unit period with reference to the tidal information.

3. The method for rearing an animal according to claim 2, further comprising, after grasping the tide-generating force:
   extracting the first timing with a relatively high variation level of the tide-generating force or the second timing with a relatively low variation level of the tide-generating force, from within the predetermined period during which the tidal information has been acquired prior to the feeding.

4. The method for rearing an animal according to claim 2, wherein the tidal information is a prediction of a periodical variation for a gravity acceleration linked with a variation in solid tide and/or for a tide level linked with a variation in marine tide.

5. An apparatus for rearing an animal, which controls an increase in body weight or fat, the apparatus comprising
   a food feeder for feeding, to the animal, foods varying in fat ingredient content according to a variation level of a tide-generating force between at a first timing and at a timing other than the first timing, or between at a second timing and at a timing other than the second timing,
   wherein the first timing is a timing of a spring tide and, at the timing of the spring tide, the animal is fed a high-fat diet food having a higher fat ingredient content than a normal diet food, which is fed at a timing other than the spring tide,
   wherein the second timing is a timing of a neap tide and, at the timing of the neap tide, the animal is fed the high-fat diet food having the higher fat ingredient content than the normal diet food, which is fed at a timing other than the neap tide, and
   wherein the variation level of the tide-generating force is within a range between a relatively-high variation level of the tide-generating force at the spring tide and a relatively-low variation level of the tide-generating force at the neap tide.

6. An apparatus for rearing an animal, which controls an increase in body weight or fat, the apparatus comprising
   a food feeder for feeding, to the animal, foods varying in fat ingredient content according to a variation level of a tide-generating force between at a first timing and at a timing other than the first timing, or between at a second timing and at a timing other than the second timing,
   wherein the first timing is a timing of a spring tide and, at the timing of the spring tide, the animal is fed a high-fat diet food having a higher fat ingredient content than a normal diet food, which is fed at a timing other than the spring tide, and
   wherein the second timing is a timing of a neap tide and, at the timing of the neap tide, the animal is fed the high-fat diet food having the higher fat ingredient content than the normal diet food, which is fed at a timing other than the neap tide, the apparatus further comprising a tide-generating force grasper for determining the variation level of the tide-generating force,
   wherein the tide-generating force grasper has:
      a tidal information acquirer for preliminarily acquiring future tidal information which, within a predetermined period, periodically varies; and
      a tide-generating force variation value calculator for calculating the variation level of the tide-generating force within a unit period with reference to the tidal information.

7. The apparatus for rearing an animal according to claim 6, further comprising a specific timing extractor for extracting the first timing showing a relatively large variation value of the tide-generating force or the second timing showing a relatively small variation value of the tide-generating force, from within the predetermined period during which the tidal information has been acquired.

8. The apparatus for rearing an animal according to claim 6, wherein the tidal information is a prediction of a periodical variation for a gravity acceleration linked with a variation in solid tide and/or for a tide level linked with a variation in marine tide.

9. The method for rearing an animal according to claim 1, wherein the variation level of the tide-generating force is within a range between a relatively-high variation level of the tide-generating force at the spring tide and a relatively-low variation level of the tide-generating force at the neap tide.

* * * * *